US012402996B2

(12) United States Patent
Felix et al.

(10) Patent No.: US 12,402,996 B2
(45) Date of Patent: Sep. 2, 2025

(54) SELF-GRIPPING HERNIA PROSTHESIS

(71) Applicant: C.R. Bard, Inc., Murray Hill, NJ (US)

(72) Inventors: Augustus Felix, Cranston, RI (US); Matthew Rothberg, Providence, RI (US); Nathan Stewart Cauldwell, Hope, RI (US); Evans Kipyego, Warwick, RI (US); Tami L. Rathbun, Exeter, RI (US); Amanda Konieczny, Naugatuck, CT (US); Joseph Paul, Thomaston, CT (US); Jeffrey E. Ransden, Fairfield, CT (US)

(73) Assignee: C.R. Bard, Inc., Murray Hill, NJ (US)

( * ) Notice: Subject to any disclaimer, the term of this patent is extended or adjusted under 35 U.S.C. 154(b) by 69 days.

(21) Appl. No.: 17/872,384

(22) Filed: Jul. 25, 2022

(65) Prior Publication Data
US 2022/0354630 A1   Nov. 10, 2022

Related U.S. Application Data

(62) Division of application No. 16/165,436, filed on Oct. 19, 2018, now Pat. No. 11,458,004.
(Continued)

(51) Int. Cl.
*A61F 2/00* (2006.01)
(52) U.S. Cl.
CPC .... *A61F 2/0063* (2013.01); *A61F 2210/0004* (2013.01); *A61F 2220/0016* (2013.01); *A61F 2230/0023* (2013.01); *A61F 2240/001* (2013.01)

(58) Field of Classification Search
CPC .............. A61F 2/0063; D10B 2509/08; A61B 2017/0647
See application file for complete search history.

(56) References Cited

U.S. PATENT DOCUMENTS

| 3,054,406 A | 9/1962 | Usher |
| 3,124,136 A | 3/1964 | Usher |

(Continued)

FOREIGN PATENT DOCUMENTS

| CN | 103705276 A | 4/2014 |
| CN | 103874465 A | 6/2014 |

(Continued)

OTHER PUBLICATIONS

International Preliminary Report on Patentability mailed Apr. 30, 2020, in connection with International Application No. PCT/US2018/056696.
(Continued)

*Primary Examiner* — Michael W Hotchkiss
(74) *Attorney, Agent, or Firm* — Wolf, Greenfield & Sacks, P.C.

(57) ABSTRACT

A self-gripping hernia prosthesis including a layer of repair fabric and a plurality of tissue grips protruding from a surface of the repair fabric. The grip may be fabricated independent of the repair fabric and subsequently attached to the layer of fabric. A backing layer may be employed to secure each grip to the repair fabric. Each base may include a base that is located between the repair fabric and the backing layer. Alternatively, the base may be attached directly to the backing layer. The tissue grips may be configured to minimize entanglement with the repair fabric.

10 Claims, 15 Drawing Sheets

Related U.S. Application Data

(60) Provisional application No. 62/574,525, filed on Oct. 19, 2017.

(56) References Cited

U.S. PATENT DOCUMENTS

| | | | |
|---|---|---|---|
| 3,320,649 A | 5/1967 | Naimer | |
| 3,494,006 A | 2/1970 | Burmlik | |
| 3,629,930 A | 12/1971 | Brumlik | |
| RE27,725 E | 8/1973 | Brumlik | |
| 3,981,051 A | 9/1976 | Brumlik | |
| 4,169,303 A | 10/1979 | Lemelson | |
| 4,338,800 A | 7/1982 | Matsuda | |
| 4,347,847 A | 9/1982 | Usher | |
| 4,452,245 A | 6/1984 | Usher | |
| 4,463,486 A | 8/1984 | Matsuda | |
| 4,520,821 A | 6/1985 | Schmidt et al. | |
| 4,653,486 A | 3/1987 | Coker | |
| 4,854,136 A | 8/1989 | Coslovi et al. | |
| 4,976,728 A | 12/1990 | Willert et al. | |
| 5,019,096 A | 5/1991 | Fox, Jr. et al. | |
| 5,032,122 A | 7/1991 | Noel et al. | |
| 5,116,357 A | 5/1992 | Eberbach | |
| 5,147,374 A | 9/1992 | Fernandez | |
| 5,176,692 A | 1/1993 | Wilk et al. | |
| 5,234,488 A | 8/1993 | Ichikawa et al. | |
| 5,254,127 A | 10/1993 | Wholey et al. | |
| 5,254,133 A | 10/1993 | Seid | |
| 5,258,000 A | 11/1993 | Gianturco | |
| 5,330,445 A | 7/1994 | Haaga | |
| 5,356,432 A | 10/1994 | Rutkow et al. | |
| 5,378,522 A | 1/1995 | Lagomarsino | |
| 5,383,897 A | 1/1995 | Wholey | |
| 5,569,273 A | 10/1996 | Titone et al. | |
| 5,634,931 A | 6/1997 | Kugel | |
| 5,643,295 A | 7/1997 | Yoon | |
| 5,716,408 A | 2/1998 | Eldridge et al. | |
| 5,716,409 A | 2/1998 | Debbas | |
| 5,761,775 A | 6/1998 | Legome et al. | |
| 5,769,864 A | 6/1998 | Kugel | |
| 5,836,961 A | 11/1998 | Kieturakis et al. | |
| 5,906,617 A | 5/1999 | Meislin | |
| 5,916,225 A | 6/1999 | Kugel | |
| 6,042,534 A | 3/2000 | Gellman et al. | |
| 6,090,116 A | 7/2000 | D'Aversa et al. | |
| 6,176,863 B1 | 1/2001 | Kugel et al. | |
| 6,224,616 B1 | 5/2001 | Kugel | |
| 6,241,747 B1 | 6/2001 | Ruff | |
| 6,280,453 B1 | 8/2001 | Kugel et al. | |
| 6,287,316 B1 | 9/2001 | Agarwal et al. | |
| 6,290,708 B1 | 9/2001 | Kugel et al. | |
| 6,312,442 B1 | 11/2001 | Kieturakis et al. | |
| 6,319,264 B1 | 11/2001 | Tormala et al. | |
| 6,383,201 B1 | 5/2002 | Dong | |
| 6,425,924 B1 | 7/2002 | Rousseau | |
| 6,468,314 B2 * | 10/2002 | Schwartz | A61F 2/30749 623/23.72 |
| 6,485,503 B2 | 11/2002 | Jacobs et al. | |
| 6,530,933 B1 | 3/2003 | Yeung et al. | |
| 6,565,590 B2 | 5/2003 | Kieturakis et al. | |
| 6,592,515 B2 | 7/2003 | Thierfelder et al. | |
| 6,596,002 B2 | 7/2003 | Therin et al. | |
| 6,596,304 B1 | 7/2003 | Bayon et al. | |
| 6,599,318 B1 | 7/2003 | Gabbay | |
| 6,645,226 B1 | 11/2003 | Jacobs et al. | |
| 6,679,900 B2 | 1/2004 | Kieturakis et al. | |
| 6,695,856 B2 | 2/2004 | Kieturakis et al. | |
| 6,740,122 B1 * | 5/2004 | Pajotin | A61F 2/0063 606/151 |
| 6,746,458 B1 | 6/2004 | Cloud | |
| 6,758,853 B2 | 7/2004 | Kieturakis et al. | |
| 6,790,213 B2 | 9/2004 | Cherok et al. | |
| 6,837,078 B1 | 1/2005 | Rock et al. | |
| 6,884,212 B2 | 4/2005 | Thierfelder et al. | |
| 6,893,452 B2 | 5/2005 | Jacobs | |
| 6,991,643 B2 | 1/2006 | Saadat | |
| 7,060,103 B2 | 6/2006 | Carr, Jr. et al. | |
| 7,083,648 B2 | 8/2006 | Yu et al. | |
| 7,094,261 B2 | 8/2006 | Zotti et al. | |
| 7,112,209 B2 | 9/2006 | Ramshaw et al. | |
| 7,156,862 B2 | 1/2007 | Jacobs et al. | |
| 7,172,615 B2 | 2/2007 | Morriss et al. | |
| 7,214,236 B2 | 5/2007 | Kieturakis et al. | |
| 7,255,675 B2 | 8/2007 | Gertner et al. | |
| 7,273,497 B2 | 9/2007 | Ferree | |
| 7,331,199 B2 | 2/2008 | Ory et al. | |
| 7,351,250 B2 | 4/2008 | Zamierowski | |
| 7,381,211 B2 | 6/2008 | Zamierowski | |
| 7,404,819 B1 | 7/2008 | Darios et al. | |
| 7,410,495 B2 | 8/2008 | Zamierowski | |
| 7,413,569 B2 | 8/2008 | Sogaard-Andersen | |
| 7,413,570 B2 | 8/2008 | Zamierowski | |
| 7,413,571 B2 | 8/2008 | Zamierowski | |
| 7,497,864 B2 | 3/2009 | Bonutti | |
| 7,510,566 B2 | 3/2009 | Jacobs et al. | |
| 7,517,313 B2 | 4/2009 | Thierfelder et al. | |
| 7,544,213 B2 | 6/2009 | Adams | |
| 7,566,337 B2 | 7/2009 | Sogaard-Andersen et al. | |
| 7,658,749 B2 | 2/2010 | Wittmann | |
| 7,662,169 B2 | 2/2010 | Wittmann | |
| 7,722,528 B2 | 5/2010 | Arnal et al. | |
| 7,905,825 B2 | 3/2011 | Arnal et al. | |
| 8,047,981 B2 | 11/2011 | Rao et al. | |
| 8,062,331 B2 | 11/2011 | Zamierowski | |
| 8,070,773 B2 | 12/2011 | Zamierowski | |
| 8,123,781 B2 | 2/2012 | Zamierowski | |
| 8,128,655 B2 | 3/2012 | Wittmann | |
| 8,157,722 B2 | 4/2012 | Arnal et al. | |
| 8,188,834 B2 | 5/2012 | Berres | |
| 8,216,273 B1 | 7/2012 | Goraltchouk et al. | |
| 8,273,105 B2 | 9/2012 | Cohen et al. | |
| 8,435,307 B2 | 5/2013 | Paul | |
| 8,454,653 B2 | 6/2013 | Hadba et al. | |
| 8,460,338 B2 | 6/2013 | Goraltchouk et al. | |
| 8,469,996 B2 | 6/2013 | Wittmann | |
| 8,500,759 B2 | 8/2013 | Koyfman et al. | |
| 8,562,644 B2 | 10/2013 | Yuan et al. | |
| 8,579,924 B2 | 11/2013 | Stopek et al. | |
| 8,585,576 B2 | 11/2013 | Arnal et al. | |
| 8,585,721 B2 | 11/2013 | Kirsch | |
| 8,615,856 B1 | 12/2013 | Gelbart | |
| 8,618,096 B2 | 12/2013 | Renslo et al. | |
| 8,632,567 B2 | 1/2014 | Cohen et al. | |
| 8,632,839 B2 | 1/2014 | Stopek et al. | |
| 8,690,960 B2 | 4/2014 | Hotter et al. | |
| 8,739,389 B2 | 6/2014 | Cohen et al. | |
| 8,747,436 B2 | 6/2014 | Nawrocki et al. | |
| 8,793,863 B2 | 8/2014 | Hunter et al. | |
| 8,821,539 B2 | 9/2014 | Rousseau | |
| 8,888,810 B2 | 11/2014 | Hadba et al. | |
| 8,906,046 B2 | 12/2014 | Anderson | |
| 8,932,327 B2 | 1/2015 | Kosa et al. | |
| 8,932,329 B2 | 1/2015 | Hadba et al. | |
| 8,961,850 B2 | 2/2015 | Wood et al. | |
| 8,968,418 B2 | 3/2015 | Paul | |
| 9,034,011 B2 | 5/2015 | Kirsch et al. | |
| 9,050,082 B2 | 6/2015 | Cohen et al. | |
| 9,060,767 B2 | 6/2015 | Bonutti | |
| 9,186,235 B2 | 11/2015 | Ory et al. | |
| 9,186,236 B2 | 11/2015 | Paul | |
| 9,295,538 B2 | 3/2016 | Koyfman et al. | |
| 9,308,068 B2 | 4/2016 | Spinnler et al. | |
| 9,358,002 B2 | 6/2016 | Kirsch et al. | |
| 9,398,943 B2 | 7/2016 | Criscuolo et al. | |
| 9,439,749 B2 | 9/2016 | Lecuivre et al. | |
| 9,445,883 B2 | 9/2016 | Lecuivre et al. | |
| 9,452,038 B2 | 9/2016 | Amal et al. | |
| 9,480,547 B2 | 11/2016 | Paul | |
| 9,510,927 B2 | 12/2016 | Simons | |
| 9,510,931 B2 | 12/2016 | Hotter et al. | |
| 9,598,801 B2 | 3/2017 | Lecuivre | |
| 9,629,703 B2 | 4/2017 | Paul | |
| 9,677,208 B2 | 6/2017 | Meneghin | |
| 9,713,467 B2 | 7/2017 | Cohen et al. | |

(56) References Cited

U.S. PATENT DOCUMENTS

| | | |
|---|---|---|
| 9,744,019 B2 | 8/2017 | Montanari et al. |
| 9,744,919 B2 | 8/2017 | Schutz |
| 9,750,595 B2 | 9/2017 | Thomas et al. |
| 9,788,832 B2 | 10/2017 | Hadba et al. |
| 9,801,703 B2 | 10/2017 | Rao et al. |
| 9,949,815 B2 | 4/2018 | Priewe |
| 9,962,162 B2 | 5/2018 | Bonutti |
| 9,962,250 B2 | 5/2018 | Priewe et al. |
| 10,052,184 B2 | 8/2018 | Deichmann et al. |
| 10,058,326 B2 | 8/2018 | Kirsch et al. |
| 10,136,984 B2 * | 11/2018 | Fischer ................ A61B 17/064 |
| 2001/0010023 A1 * | 7/2001 | Schwartz ............ A61F 2/30749 623/23.72 |
| 2002/0022861 A1 | 2/2002 | Jacobs et al. |
| 2002/0058966 A1 | 5/2002 | Tormala et al. |
| 2002/0077661 A1 * | 6/2002 | Saadat ...................... A61F 2/08 606/221 |
| 2002/0103494 A1 | 8/2002 | Pacey |
| 2002/0169452 A1 | 11/2002 | Tormala et al. |
| 2002/0188170 A1 | 12/2002 | Santamore et al. |
| 2003/0036801 A1 | 2/2003 | Schwartz et al. |
| 2003/0069602 A1 | 4/2003 | Jacobs et al. |
| 2003/0074021 A1 * | 4/2003 | Morriss ................. A61F 2/0059 606/215 |
| 2003/0105477 A1 * | 6/2003 | Schwartz ............ A61F 2/30749 606/151 |
| 2003/0187516 A1 * | 10/2003 | Amid .................... A61B 90/92 623/23.72 |
| 2004/0059356 A1 | 3/2004 | Gingras |
| 2004/0138683 A1 * | 7/2004 | Shelton .............. A61B 17/0401 606/232 |
| 2004/0138705 A1 | 7/2004 | Heino et al. |
| 2004/0204723 A1 | 10/2004 | Kayan |
| 2004/0215219 A1 | 10/2004 | Eldridge et al. |
| 2004/0260340 A1 | 12/2004 | Jacobs et al. |
| 2005/0021058 A1 | 1/2005 | Negro |
| 2005/0085924 A1 | 4/2005 | Darois et al. |
| 2005/0113858 A1 | 5/2005 | Deutsch |
| 2005/0119694 A1 | 6/2005 | Jacobs et al. |
| 2005/0216042 A1 | 9/2005 | Gertner |
| 2005/0222591 A1 | 10/2005 | Gingras et al. |
| 2005/0228408 A1 | 10/2005 | Fricke et al. |
| 2006/0089672 A1 | 4/2006 | Martinek |
| 2006/0141012 A1 | 6/2006 | Gingras |
| 2006/0173471 A1 | 8/2006 | Carr et al. |
| 2006/0200062 A1 | 9/2006 | Saadat |
| 2006/0205995 A1 | 9/2006 | Browning |
| 2006/0253132 A1 | 11/2006 | Evans et al. |
| 2006/0253203 A1 | 11/2006 | Alvarado |
| 2006/0282103 A1 | 12/2006 | Fricke et al. |
| 2007/0027358 A1 | 2/2007 | Gertner et al. |
| 2007/0068538 A1 | 3/2007 | Anderson et al. |
| 2007/0083229 A1 | 4/2007 | Deutsch |
| 2007/0123936 A1 | 5/2007 | Goldin et al. |
| 2007/0260268 A1 | 11/2007 | Bartee et al. |
| 2007/0265704 A1 * | 11/2007 | Mayer .................. A61F 2/0063 623/11.11 |
| 2008/0009902 A1 | 1/2008 | Hunter et al. |
| 2008/0033461 A1 | 2/2008 | Koeckerling et al. |
| 2008/0113001 A1 * | 5/2008 | Herweck ................ A61L 31/14 424/445 |
| 2008/0195231 A1 | 8/2008 | Ory et al. |
| 2008/0200950 A1 | 8/2008 | Wohlert |
| 2008/0206305 A1 | 8/2008 | Herweck et al. |
| 2008/0208079 A1 | 8/2008 | Hein et al. |
| 2008/0255593 A1 | 10/2008 | St-Germain |
| 2008/0281357 A1 | 11/2008 | Sung et al. |
| 2009/0024147 A1 | 1/2009 | Ralph et al. |
| 2009/0082792 A1 | 3/2009 | Koyfman et al. |
| 2009/0112236 A1 | 4/2009 | Stopek |
| 2009/0163938 A1 | 6/2009 | Bonutti |
| 2009/0187197 A1 | 7/2009 | Roeber et al. |
| 2009/0192532 A1 | 7/2009 | Spinnler et al. |
| 2009/0204129 A1 | 8/2009 | Fronio |
| 2009/0216075 A1 | 8/2009 | Bell et al. |
| 2009/0216338 A1 | 8/2009 | Gingras et al. |
| 2009/0228021 A1 | 9/2009 | Leung |
| 2009/0240267 A1 | 9/2009 | Crawley et al. |
| 2009/0240343 A1 | 9/2009 | Adams |
| 2009/0248067 A1 | 10/2009 | Maiorino |
| 2009/0248070 A1 | 10/2009 | Kosa et al. |
| 2009/0299407 A1 | 12/2009 | Yuan et al. |
| 2009/0306681 A1 | 12/2009 | Del Nido et al. |
| 2010/0191044 A1 | 7/2010 | Gobron et al. |
| 2010/0211097 A1 | 8/2010 | Hadba et al. |
| 2010/0255447 A1 | 10/2010 | Biris et al. |
| 2010/0268272 A1 | 10/2010 | Kirsch et al. |
| 2010/0274283 A1 | 10/2010 | Kirsch et al. |
| 2010/0292719 A1 | 11/2010 | Ducharme |
| 2011/0028995 A1 | 2/2011 | Miraki et al. |
| 2011/0077457 A1 * | 3/2011 | Deitch .................. A61F 2/0045 600/37 |
| 2011/0082478 A1 | 4/2011 | Glick et al. |
| 2011/0130774 A1 | 6/2011 | Criscuolo et al. |
| 2011/0160527 A1 | 6/2011 | Khamis et al. |
| 2011/0172760 A1 | 7/2011 | Anderson |
| 2011/0238094 A1 | 9/2011 | Thomas et al. |
| 2011/0276090 A1 | 11/2011 | Berndt et al. |
| 2011/0282365 A1 | 11/2011 | Hadba et al. |
| 2011/0282386 A1 | 11/2011 | Friedrich et al. |
| 2011/0288565 A1 | 11/2011 | Kubiak et al. |
| 2011/0288566 A1 | 11/2011 | Kubiak |
| 2012/0010637 A1 | 1/2012 | Stopek et al. |
| 2012/0027804 A1 | 2/2012 | Odermatt et al. |
| 2012/0029538 A1 * | 2/2012 | Reeser ................. A61B 17/068 606/151 |
| 2012/0053399 A1 | 3/2012 | Rao et al. |
| 2012/0082712 A1 | 4/2012 | Stopek et al. |
| 2012/0094004 A1 | 4/2012 | Stopek et al. |
| 2012/0094005 A1 | 4/2012 | Stopek et al. |
| 2012/0165937 A1 | 6/2012 | Montanari et al. |
| 2012/0172926 A1 | 7/2012 | Hotter |
| 2012/0179175 A1 | 7/2012 | Hammell |
| 2012/0197415 A1 * | 8/2012 | Montanari ............... A61L 27/56 623/23.74 |
| 2012/0310278 A1 | 12/2012 | Marczyk et al. |
| 2012/0330093 A1 | 12/2012 | Odermatt et al. |
| 2013/0018393 A1 | 1/2013 | Bengston |
| 2013/0102959 A1 | 4/2013 | Stopek et al. |
| 2013/0103060 A1 | 4/2013 | Stopek et al. |
| 2013/0138124 A1 | 5/2013 | Criscuolo et al. |
| 2013/0158571 A1 * | 6/2013 | Meneghin .............. D04B 21/12 606/151 |
| 2013/0158572 A1 | 6/2013 | Meneghin et al. |
| 2013/0172915 A1 | 7/2013 | Thomas et al. |
| 2013/0172927 A1 * | 7/2013 | Natarajan ............. A61F 2/0077 264/319 |
| 2013/0184722 A1 | 7/2013 | Stopek et al. |
| 2013/0190785 A1 | 7/2013 | Koyfman et al. |
| 2013/0204277 A1 | 8/2013 | Fabry et al. |
| 2013/0218125 A1 | 8/2013 | Stopek et al. |
| 2013/0231688 A1 | 9/2013 | Paul |
| 2013/0231702 A1 | 9/2013 | Hadba et al. |
| 2013/0261542 A1 | 10/2013 | Elachchabi et al. |
| 2013/0261594 A1 | 10/2013 | Stopek et al. |
| 2013/0331792 A1 | 12/2013 | Karp et al. |
| 2014/0046348 A1 * | 2/2014 | Soltanian ............. A61B 17/064 606/151 |
| 2014/0066958 A1 | 3/2014 | Priewe |
| 2014/0081295 A1 | 3/2014 | Lau et al. |
| 2014/0094829 A1 | 4/2014 | Kostrzewski |
| 2014/0094830 A1 * | 4/2014 | Sargeant ............... A61F 2/0063 606/151 |
| 2014/0094831 A1 | 4/2014 | Thomas et al. |
| 2014/0142368 A1 | 5/2014 | Arnal et al. |
| 2014/0142520 A1 | 5/2014 | Stopek et al. |
| 2014/0148827 A1 * | 5/2014 | Odermatt ........... A61B 17/0057 606/151 |
| 2014/0222164 A1 | 8/2014 | Hotter et al. |
| 2014/0224094 A1 | 8/2014 | Cohen et al. |
| 2014/0228867 A1 * | 8/2014 | Thomas ................ A61F 2/0063 264/293 |

(56) References Cited

U.S. PATENT DOCUMENTS

| | | |
|---|---|---|
| 2014/0257348 A1 | 9/2014 | Priewe et al. |
| 2014/0257517 A1 | 9/2014 | Deichmann et al. |
| 2015/0012089 A1 | 1/2015 | Shetty et al. |
| 2015/0040534 A1 | 2/2015 | Hadba et al. |
| 2015/0057762 A1* | 2/2015 | Harms .................... A61F 2/02 623/23.74 |
| 2015/0080918 A1* | 3/2015 | Lecuivre ............... D04B 21/12 606/151 |
| 2015/0119933 A1 | 4/2015 | Kosa et al. |
| 2015/0133998 A1 | 5/2015 | Cohen et al. |
| 2015/0196378 A1* | 7/2015 | Mayer ............... A61B 17/8605 606/151 |
| 2015/0245837 A1 | 9/2015 | Bonutti |
| 2015/0313700 A1* | 11/2015 | Rizk .................... A61F 2/0063 606/151 |
| 2015/0315729 A1* | 11/2015 | Simons ................. D04B 21/12 66/170 |
| 2016/0022405 A1 | 1/2016 | Spinnler et al. |
| 2016/0135969 A1* | 5/2016 | Anderson ......... A61B 17/0644 623/1.18 |
| 2016/0262749 A1 | 9/2016 | Kirsch et al. |
| 2016/0374791 A1 | 12/2016 | Lecuivre et al. |
| 2016/0374792 A1 | 12/2016 | Lecuivre et al. |
| 2017/0105724 A1* | 4/2017 | Limem ................ A61B 17/064 |
| 2017/0189158 A1 | 7/2017 | Lecuivre |
| 2017/0202654 A1 | 7/2017 | Paul |
| 2017/0209251 A1* | 7/2017 | Francois ............... A61F 2/0063 |
| 2017/0231740 A1* | 8/2017 | Peery .................. A61B 17/064 606/151 |
| 2017/0296319 A1* | 10/2017 | Peery .................. A61B 17/068 |
| 2017/0319203 A1 | 11/2017 | Cohen et al. |
| 2018/0008390 A1 | 1/2018 | Montanari et al. |
| 2018/0161141 A1 | 6/2018 | Priewe et al. |
| 2018/0235740 A1 | 8/2018 | Deichmann et al. |
| 2018/0250007 A1 | 9/2018 | Bonutti |
| 2018/0318057 A1* | 11/2018 | Bailly .................. A61F 2/0063 |
| 2018/0325518 A1* | 11/2018 | Tannhauser ...... A61B 17/07292 |
| 2019/0117363 A1 | 4/2019 | Felix et al. |

FOREIGN PATENT DOCUMENTS

| | | |
|---|---|---|
| DE | 198 32 634 A1 | 1/2000 |
| EP | 0 276 890 A2 | 8/1988 |
| EP | 1 274 892 B1 | 11/2009 |
| EP | 2 143 836 A1 | 1/2010 |
| EP | 2 229 918 A1 | 9/2010 |
| EP | 2 514 862 A2 | 10/2012 |
| EP | 2 567 715 A1 | 3/2013 |
| EP | 2 712 577 A1 | 4/2014 |
| EP | 2 753 370 B1 | 1/2016 |
| EP | 2 744 934 B1 | 10/2018 |
| EP | 2 798 105 B1 | 10/2018 |
| EP | 2 798 106 B1 | 10/2018 |
| FR | 2 712 177 A1 | 5/1995 |
| WO | WO 2006/116000 A2 | 11/2006 |
| WO | WO 2007/120138 A2 | 10/2007 |
| WO | WO 2009/132284 A2 | 10/2009 |
| WO | WO 2012/007579 A1 | 1/2012 |
| WO | WO 2013/026682 A1 | 2/2013 |
| WO | WO 2013/034641 A1 | 3/2013 |
| WO | WO 2013/049799 A1 | 4/2013 |
| WO | WO 2013/098343 A1 | 7/2013 |
| WO | WO 2013/098345 A1 | 7/2013 |
| WO | WO 2013/098347 A1 | 7/2013 |
| WO | WO 2013/139482 A1 | 9/2013 |
| WO | WO 2014/001432 A1 | 1/2014 |
| WO | WO 2014/048922 A1 | 4/2014 |
| WO | WO 2014/139633 A1 | 9/2014 |
| WO | WO 2014/139635 A1 | 9/2014 |
| WO | WO 2016/141183 A1 | 9/2016 |

OTHER PUBLICATIONS

International Search Report and Written Opinion mailed Feb. 11, 2019, in connection with International Application No. PCT/US2018/056696.
Chinese Office Action mailed Feb. 16, 2022, in connection with Chinese Application No. 201880074867.8.
Chinese Office Action mailed Sep. 9, 2022, in connection with Chinese Application No. 201880074867.8.

* cited by examiner

SELF-GRIPPING HERNIA PROSTHESIS

RELATED APPLICATIONS

This application is a divisional of U.S. application Ser. No. 16/165,436, filed Oct. 19, 2018, which claims the benefit of U.S. Provisional Application No. 62/574,525, filed Oct. 19, 2017, each of which is incorporated herein by reference in its entirety.

FIELD

The present invention relates to an implantable prosthesis, and more particularly to a prosthesis for mending defects and weaknesses of soft tissue and muscle walls.

BACKGROUND

A defect in a muscle or tissue wall, such as a hernia, is commonly repaired with an implantable prosthesis that is configured to cover and/or fill the defect.

For some procedures, an implantable repair fabric, such as a mesh fabric, is sutured, stapled, tacked, or otherwise provisionally anchored in place over, under or within the defect. Tissue integration with the fabric, such as tissue ingrowth into and/or along the mesh fabric, eventually completes the repair.

Various repair fabrics are known and used for repairing soft tissue and muscle wall defects. Examples of implantable fabrics that have been successfully used in soft tissue and muscle wall repair include BARD Soft Mesh, BARD Mesh and VISILEX, available from C. R. Bard. Such fabrics are fabricated from polypropylene monofilaments that are knitted into a mesh having pores or interstices that promote tissue ingrowth and integration with the fabric.

For some procedures, it may be desirable to employ an implantable prosthesis configured to fit the shape of the anatomical region of the defect. In some instances, such a prosthesis can be positioned and maintain its position relative to the defect with little or no provisional fixation. Examples of implantable prostheses that have been successfully used in soft tissue and muscle wall repair include 3DMAX Light Mesh and 3DMAX Mesh, available from C. R. Bard. Such prostheses are fabricated from a mesh fabric formed into a curved, 3-dimensional shape that fits the anatomical shape of the defect region, such as the inguinal anatomy. These prostheses have proven useful and have become established in the practice of muscle or tissue wall repair in the inguinofemoral region.

It is an object of the invention to provide a prosthesis for mending defects in soft tissue and muscle walls.

SUMMARY

The present invention relates to an implantable prosthesis for mending an anatomical defect, such as a tissue or muscle wall defect, including a groin defect.

According to one aspect, an implantable prosthesis comprises a first layer of biologically compatible repair fabric, a second layer of biologically compatible repair fabric attached to the first layer, and a plurality of tissue grips protruding from a first surface of the first layer. The plurality of grips are independent of the first layer and secured to the first layer with the second layer.

According to another aspect, an implantable prosthesis comprises a first layer of biologically compatible repair fabric and a plurality of tissue grips protruding from a first surface of the first layer. The plurality of grips are configured to penetrate and grip tissue. Each tissue grip includes a grip body protruding from the first layer and a grip head located at an end of the grip body spaced away from the first surface of the first layer. The grip head includes a first pair of barbs located along a first axis oriented in a first radial direction and a second pair of barbs located along a second axis oriented in a second radial direction that is different from the first radial direction.

According to another aspect, an implantable prosthesis comprises a first layer of biologically compatible repair fabric and a plurality of tissue grips protruding from a first surface of the first layer. The plurality of grips are configured to penetrate and grip tissue. Each tissue grip includes a grip body protruding from the first layer and a grip head located at an end of the grip body spaced away from the first surface of the first layer. The grip head includes a plurality of primary barbs and a plurality of secondary barbs with the primary barbs being different from the secondary barbs. The primary barbs are configured to minimize entanglement of the grip head with the repair fabric. The primary barbs may be positioned to shield the secondary barbs from entanglement.

According to another aspect, a method is provided for fabricating an implantable prosthesis. The method comprises acts of: (a) providing a first layer of biologically compatible repair fabric including a first surface and a second surface opposite the first surface, and (b) attaching a plurality of tissue grips to the first layer of repair fabric. The plurality of grips are fabricated independent of the first layer. Each tissue grip includes a grip base and a grip body extending from the grip base. The grips are attached to the first layer by passing the grip body through the first layer to protrude beyond the first surface and positioning the grip base adjacent the second surface.

The foregoing is a non-limiting summary of the invention, which is defined by the attached claims. Other aspects, embodiments and/or features will become apparent from the following description.

Various embodiments of the present invention may provide certain advantages and may overcome certain drawbacks of prior prostheses. Embodiments of the invention may not share the same advantages, and those that do may not share them under all circumstances.

BRIEF DESCRIPTION OF DRAWINGS

Aspects of the invention are described below, by way of example, with reference to the accompanying drawings in which like numerals reference like elements, and wherein.

DETAILED DESCRIPTION

Figure 1:
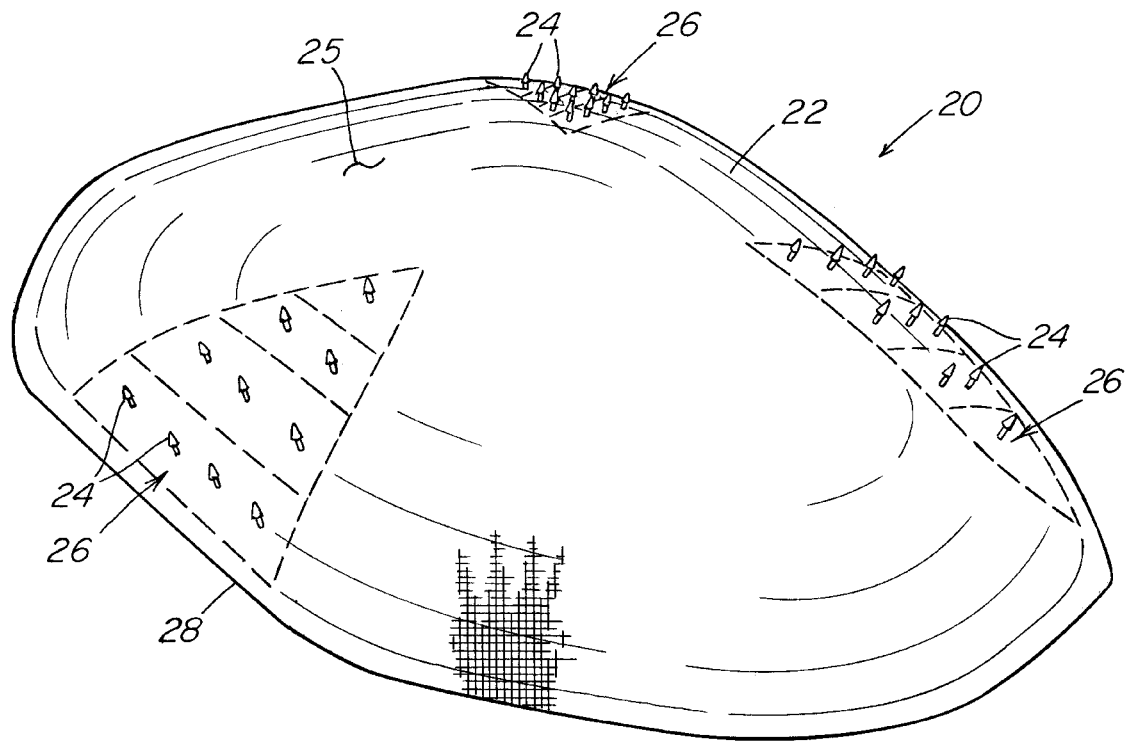
FIG. 1 is an end perspective view of an implantable prosthesis according to one embodiment.
Figure 2:
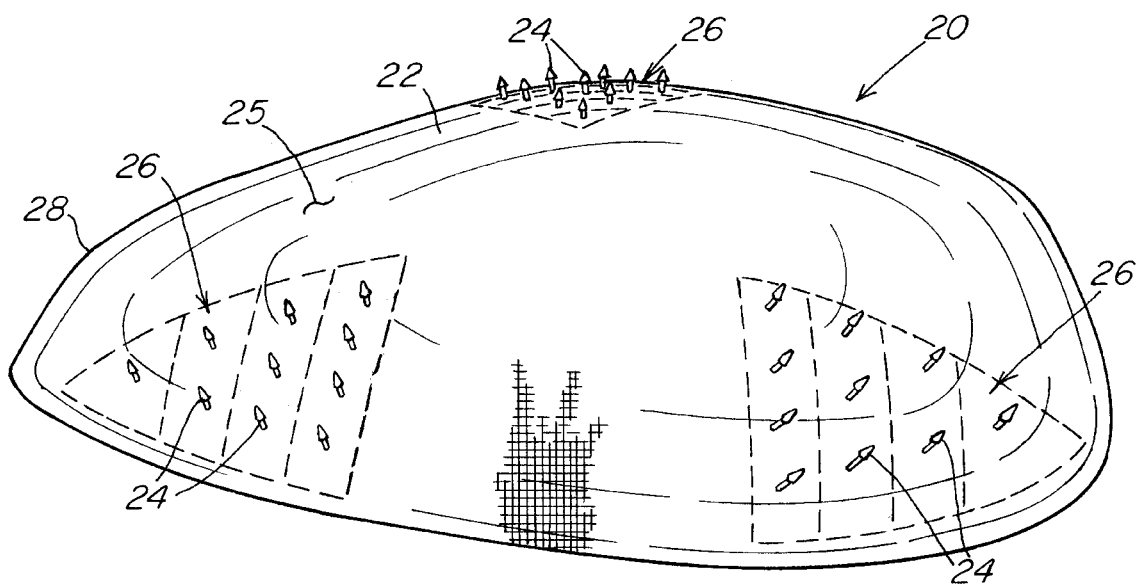
FIG. 2 is a side perspective view of the implantable prosthesis of FIG. 1.
Figure 3:
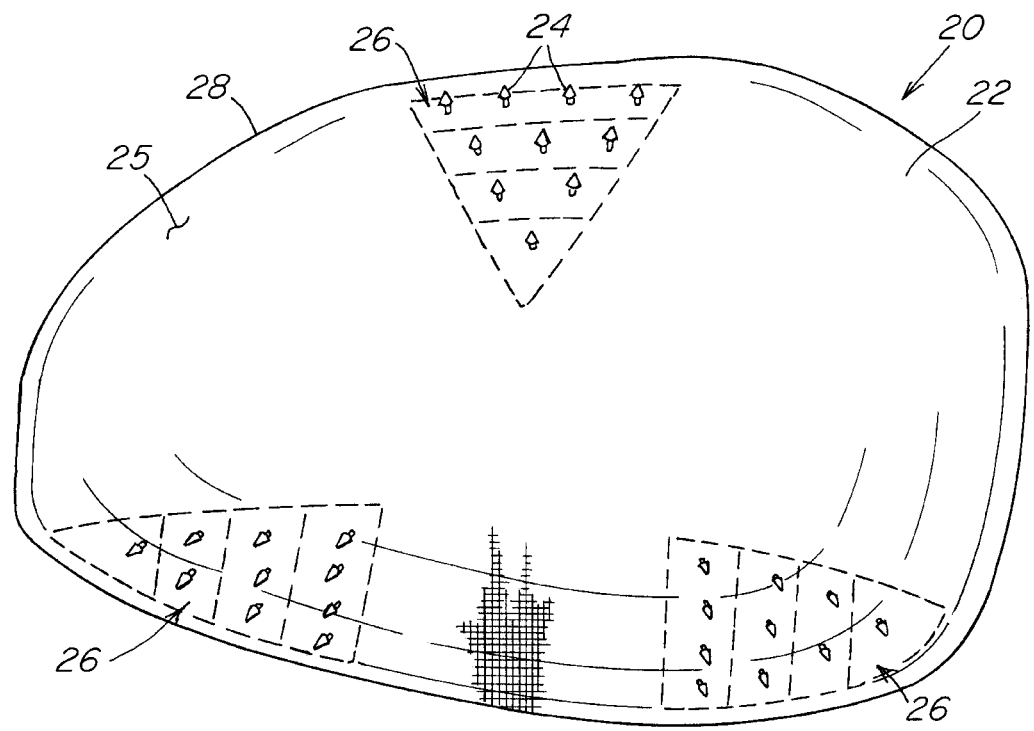
FIG. 3 is a top view of the implantable prosthesis of FIG. 1.
Figure 4:
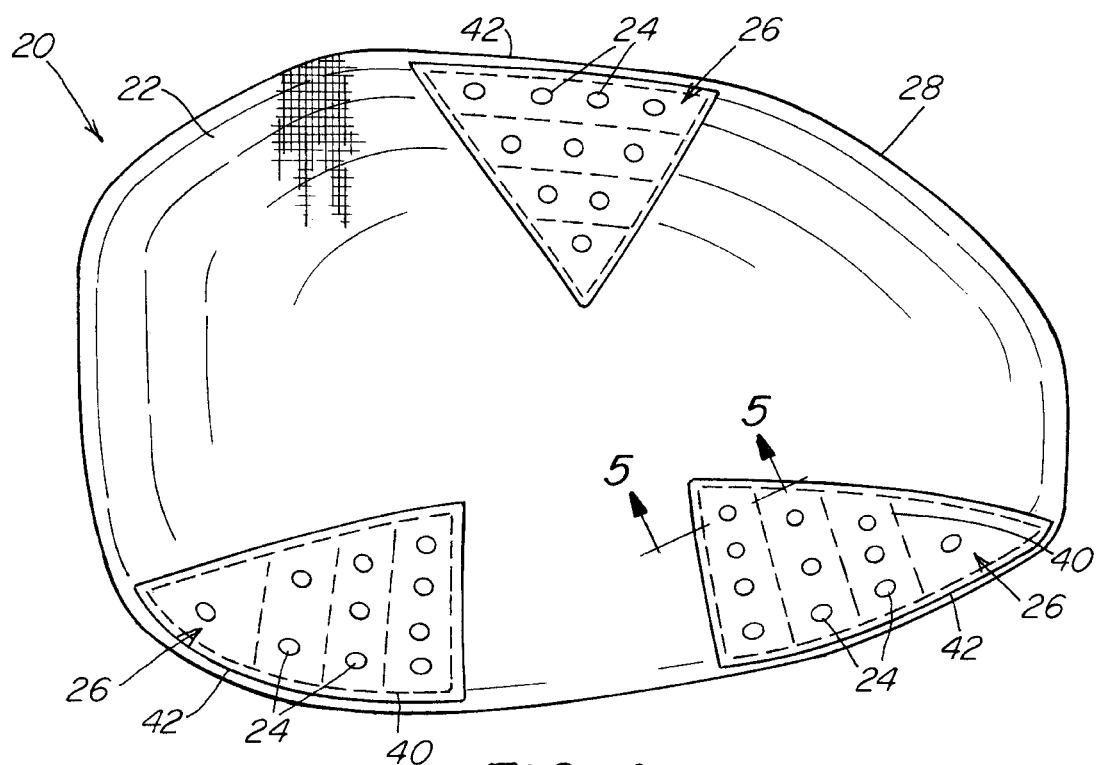
FIG. 4 is a bottom view of the implantable prosthesis of FIG. 1.

It should be understood that aspects of the invention are described herein with reference to the figures, which show illustrative embodiments in accordance with aspects of the invention. The illustrative embodiments described herein are not necessarily intended to show all aspects of the invention, but rather are used to describe a few illustrative embodiments. Thus, aspects of the invention are not intended to be construed narrowly in view of the illustrative embodiments. It should be appreciated, then, that the various concepts and embodiments discussed herein may be implemented in any of numerous ways, as the disclosed concepts and embodiments are not limited to any particular manner of implementation. In addition, it should be understood that aspects of the invention may be used alone or in any suitable combination with other aspects of the invention.

The invention is directed to an implantable prosthesis for mending an anatomical defect, and is particularly suitable for mending defects in, and weaknesses of, soft tissue and muscle walls or other anatomical regions. The phrase "mending a defect" includes acts of repairing, augmenting, and/or reconstructing a defect and/or a potential defect. For ease of understanding, and without limiting the scope of the invention, the prosthesis is described below particularly in connection with mending a groin defect including, but not limited to, one or more of an indirect inguinal hernia, a direct inguinal hernia, a femoral hernia and/or other weakness or rupture of the groin anatomy. It should be understood, however, that the prosthesis is not so limited and may be employed in other anatomical procedures, as should be apparent to one of skill in the art. For example, and without limitation, the prosthesis may be employed for ventral hernias, chest or abdominal wall reconstruction, or large defects, such as those that may occur in obese patients. The prosthesis may include one or more features, each independently or in combination, contributing to such attributes.

The invention is more particularly directed to a prosthesis which includes a repair fabric having a body portion that is configured to cover or extend across the defect opening or weakness when the body portion is placed against the defect. The prosthesis may be in the form of a patch, although the prosthesis may employ other configurations as should be apparent to one of skill in the art. The patch may have a planar or non-planar configuration suitable for a particular procedure employed for mending a defect.

The prosthesis may be configured with a self-grip arrangement having features that help maintain the position of the prosthesis relative to the defect. The self-grip arrangement may reduce, if not eliminate, separation, sliding, twisting, folding and/or other movement, as may be desired, between the prosthesis and adjacent tissue. Such an arrangement may also reduce, if not eliminate, the need for a surgeon to suture, staple, tack, or otherwise provisionally anchor the prosthesis in place pending tissue integration.

The prosthesis may include a plurality of grips protruding from the body portion. More particularly, the grips may protrude from a surface of the body portion that is configured to engage adjacent tissue. The grips may be configured to penetrate and grip the tissue when the prosthesis is placed and/or pressed against it. In this manner, the grips may be configured to protrude a defined distance from the surface of the body portion to penetrate a depth of tissue sufficient to provide the desired amount of grip.

The grips may be arranged on the body portion in any suitable configuration to provide a desired amount of grip as should be apparent to one of skill in the art. For example, and without limitation, the grips may be distributed across the body portion in a uniform, non-uniform or random array, and/or any suitable combination of arrays. The grips may be distributed across the entire body portion or located at one or more select regions of the body portion. For example, and without limitation, the grips may be located at one or more select regions adjacent one or more segments of the outer periphery of the body portion, and/or one or more select regions located within the inner region of the body portion inwardly away from the outer periphery. Each select region may include one or more grips arranged in any suitable pattern within the region. One or more of the select regions may employ the same or different arrangements of grips relative to one or more other select regions of grips.

According to one aspect, the grips may be fabricated independent of and mounted to the body portion of the prosthesis. In this manner, the grips may be formed from a material that is different from the body portion. For example, and without limitation, the grips may be formed of a bioabsorbable material, while the body portion may be formed of a non-absorbable material. Such an arrangement may provide the prosthesis with temporary grip properties during the period of tissue integration, while reducing the amount of foreign material that remains present in a patient's body and maintaining long-term strength of the prosthesis.

Independent fabrication of the grips may also provide flexibility for configuring the prosthesis. For example, and without limitation, the prosthesis may include grips having the same or different grip configurations and/or arrangements depending on a particular application of the prosthesis. For example, and without limitation, the prosthesis may include grips having the same shape, but mounted in different orientations relative to each other on the body portion. The prosthesis may include grips with one or more different shapes in one or more regions of the body portion. In this manner, the prosthesis may be provided with various grip characteristics based on the particular orientations and/or shapes of the grips individually and as a whole.

The grips may be directly or indirectly mounted to the body portion of the prosthesis. Each grip may include a base and a grip body extending from the base. The base may be mounted to the body portion with the grip body protruding from the body portion and configured to penetrate and grip tissue.

In one aspect, the grips may be molded or welded directly to the body portion. For example, and without limitation, each grip may be insert molded to prefabricated mesh fabric placed within a mold that receives grip material and forms the desired shape of the grip directly onto the body portion.

In one aspect, each grip may be mechanically mounted to the body portion. For example, and without limitation, each grip may be mounted using a mechanical component or arrangement that is attached to the body portion. For example, and without limitation, the body portion may include a first layer of repair fabric and a second layer of repair fabric attached to the first layer to secure the grips to the first layer. The base of each grip may be retained between the first and second layers of repair fabric. Alternatively, each grip may be mounted directly to the second layer which is subsequently attached to the first layer. Such indirect mounting arrangements may reduce the likelihood of potential degradation of the strength and/or tissue infiltration characteristics of the first layer. In another non-limiting example, the base of each grip may be configured to mechanically connect with the repair fabric of the body portion.

The grip may include a grip head located at the end of the grip body opposite the base that is configured for insertion into tissue while providing a sufficient amount of tissue grip to reduce, if not eliminate, inadvertent release from the tissue. The grip head may also be configured to minimize, if not eliminate, potential entanglement with the prosthesis, such as a mesh repair fabric, while providing desired tissue grip. For example, and without limitation, the grip head may include one or more barbs of any suitable configuration as should be apparent to one of skill in the art. The grip head may include barbs having different configuration relative to each other. For example, and without limitation, a first barb configuration may be suitable for tissue grip while minimizing entanglement and a second barb configuration may be suitable for just gripping tissue. The grip head configurations may include, but are not be limited to, an arrowhead shape, a crescent shape, multiple prongs arranged in a V-shape, and a claw shape. Other grip head configurations are also contemplated.

The prosthesis may be used for mending soft tissue and muscle wall defects using various surgical techniques, including open, laparoscopic, hybrid (e.g., Kugel procedure), and robotic techniques. During open procedures, the prosthesis may be placed through a relatively large incision made in the abdominal wall and layers of tissue and then the defect is filled or covered with the repair fabric. During laparoscopic and hybrid procedures, the prosthesis may be collapsed, such as by rolling or folding, into a reduced configuration for entry into a subject, either directly through a comparatively smaller incision or through a slender laparoscopic cannula that is placed through the incision. The prosthesis may have particular application with robotic procedures in which placement of the prosthesis is achieved using surgical robotic tools which may involve passage of the prosthesis through a relatively small cannula (e.g., 8 mm) as compared to a cannula (e.g., 10-12 mm) typically employed for more conventional laparoscopic techniques.

FIGS. 1-4 illustrate one embodiment of a prosthesis for mending tissue and muscle wall defects, such as a hernia defect. The prosthesis includes a repair fabric of implantable, biologically compatible material. In one embodiment, the repair fabric may comprise a mesh fabric that is relatively flexible, thin and light weight and meets the performance and physical characteristics for mending soft tissue and muscle wall defects.

The prosthesis 20 may include a body portion 22 configured with a size and/or shape suitable to cover or extend across the defect opening or weakness when the body portion is placed against the defect. The prosthesis may also include a plurality of grips 24 protruding from the body portion to provide a self-grip arrangement for maintaining the position of the prosthesis relative to the defect. The grips 24 are configured to protrude from a surface 25 of the body portion for engaging adjacent tissue.

The grips 24 may be configured to penetrate and grip the tissue when the prosthesis is placed and/or pressed against it. In this manner, the grips may be configured to protrude a defined distance from the surface of the body portion to penetrate a depth of tissue sufficient to provide the desired amount of grip. In one embodiment, the grips 24 may be configured to protrude 0.05 inches to 0.15 inches from the surface. However, the grips may be configured to protrude other distances sufficient to provide a desired amount of grip as should be apparent to one of skill in the art.

In one illustrative embodiment, the grips 24 may be located at one or more grip regions 26 of the body portion. Such an arrangement may be suitable for placing grips in selected regions of the body portion to accommodate a particular anatomical region. For example, it may be desirable to avoid providing grips on regions of the body portion that may potentially contact vessels, nerves or other portions of the anatomy at the defect site as should be apparent to one of skill in the art.

As shown in FIGS. 1-4, the grip regions 26 may be located adjacent one or more segments of the outer periphery 28 of the body portion 22 and extend inwardly toward the inner region of the body portion. Each grip region 26 may include a plurality of grips 24 arranged in any suitable pattern within the region, for example, to facilitate rolling and/or folding of the prosthesis to the site of the soft tissue repair. In one illustrative embodiment, the prosthesis 20 may be provided with three grip regions 26 including grips 24 arranged in multiple rows and/or columns with the number of grips in each row and/or column decreasing in a direction away from the outer periphery. As shown, each grip region 26 may include ten grips 24 arranged in four rows and/or columns of decreasing grips. In this manner, the grips may be viewed as having a generally triangular arrangement.

It is to be appreciated that any suitable grip arrangement may be provided on the prosthesis to provide a desired amount of grip as should be apparent to one of skill in the art. For example, and without limitation, a single row of grips may be located along one or more select segments of the outer periphery. In other embodiments, one or more of the select regions may employ the same or different arrangements of grips relative to one or more other select regions of grips. The grips may be arranged in a uniform, non-uniform or random array, and/or any suitable combination of arrays. Rather than limited to one or more select grip regions, the grips may be distributed across the entire body portion.

The grips may be fabricated independent of and mounted to the body portion of the prosthesis. Independent fabrication of the grips may provide flexibility for configuring the prosthesis.

In one embodiment, the grips may be formed of a bioabsorbable material, while the body portion may be formed of a non-absorbable material. Such an arrangement may provide the prosthesis with temporary grip properties during the period of tissue integration, while reducing the amount of foreign material that remains present in a patient's body and maintaining long-term strength of the prosthesis.

In other embodiments, the prosthesis may include grips having the same or different grip configurations and/or arrangements depending on a particular application of the prosthesis. For example, and without limitation, the prosthesis may include grips having the same shape, but mounted in different orientations relative to each other on the body portion. The prosthesis may include grips with one or more different shapes in one or more regions of the body portion. In this manner, the prosthesis may be provided with various grip characteristics based on the particular orientations and/or shapes of the grips individually and as a whole.

Figure 5:
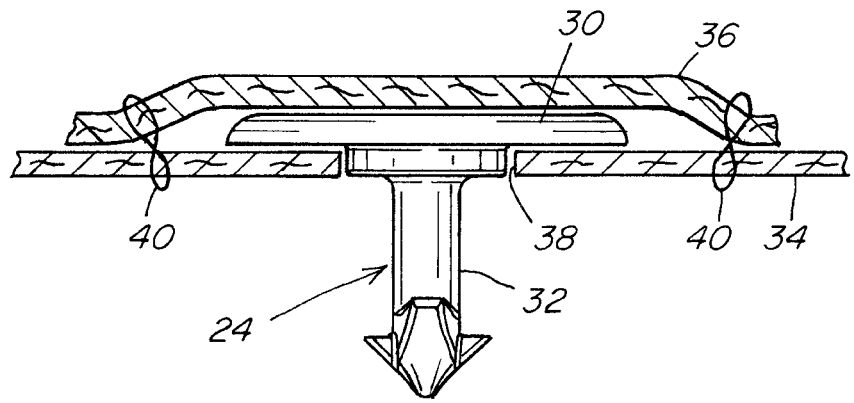
FIG. 5 is a sectional view taken along section line 5-5 of FIG. 4 illustrating a tissue grip being attached to the prosthesis according to one embodiment.

In one illustrative embodiment shown in FIG. 5, each grip 24 may include a base 30 and a grip body 32 extending from the grip base. The grip base 30 may be mounted to the body portion 22 of the prosthesis with the grip body 32 protruding from the body portion to penetrate and grip tissue. The body portion 22 of the prosthesis may include a first layer 34 of repair fabric configured to extend across and cover the defect and a second layer 36 of repair fabric attached to the first layer to secure each grip to the first layer. As shown, the base 30 of each grip may be retained between the first and second layers 34, 36 of repair fabric with the second layer 36 acting as a backing layer. The grip body 32 may extend through a pore 38 of the first layer 34 of fabric, although the prosthesis is not so limited.

In one embodiment, each backing layer 36 may be configured to correspond with the shape of each grip region 26 of the prosthesis. However, the shape of the backing layer is not so limited and may have any suitable configuration apparent to one of skill in the art.

Each backing layer 36 may be attached to the first layer 34 using any suitable fastening arrangement as should be apparent to one of skill in the art. In one embodiment, the backing layers 36 may be attached to the first layer 34 using stitches 40 extending about the outer periphery 42 of the backing layer. Additional stitches may be placed between rows and/or columns of the grips to reduce billowing of the backing layer and maintain the grips in position between the layers. It is to be appreciated that other attachment techniques may be employed including, but not limited to, bonding and ultrasonic welding.

Rather than securing the grips between layers of repair fabric, it may be desirable to directly mount the grips to a second layer for subsequent attachment to the first layer. Such an arrangement may be desirable to allow one or more grip regions of any desired configuration be trimmed from a relatively large layer of fabric having pre-attached grips. Such an indirect mounting arrangement may also reduce the incidence of potential degradation of the strength and/or tissue infiltration characteristics of the first layer.

In one illustrative embodiment shown in FIG. 6, each grip 24 may be mounted directly to the second layer 36 of fabric which is subsequently attached to the first layer 34 of fabric. As shown, the grip base 30 may be secured to the second layer 36 with the grip body 32 extending through the second layer. The grip base may be attached to the second layer using any suitable technique including, but not limited to, bonding or ultrasonic welding 44. The second layer may be attached to the first layer using any suitable fastening technique as described above.

It is to be understood that other techniques may be employed to attach tissue grips to the body portion of the prosthesis. In one embodiment, the grips may be molded or welded directly to the body portion. For example, and without limitation, each grip may be insert molded to prefabricated mesh fabric placed within a mold that receives grip material and forms the desired shape of the grip directly onto the mesh fabric. The mesh fabric may be used as the first layer 34 of the body portion or as the second layer 36 of the body portion that is attached to the first layer. In another non-limiting example, the base 30 of each grip 24 may be configured to mechanically connect with the repair fabric of the body portion.

As indicated above, the prosthesis may include grips 24 having the same or different grip configurations and/or arrangements depending on a particular application of the prosthesis.

Figure 6:
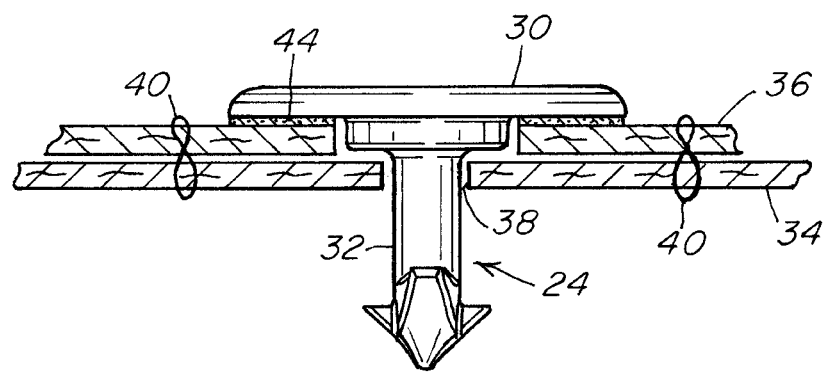
FIG. 6 is a sectional view taken along section line 5-5 of FIG. 4 illustrating a tissue grip being attached to the prosthesis according to another embodiment.
Figure 7:
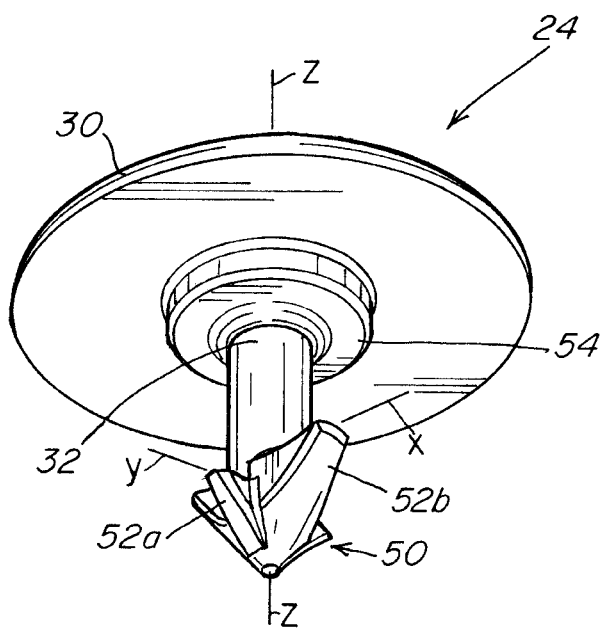
FIG. 7 is a perspective view of a tissue grip of FIGS. 5-6 according to one illustrative embodiment.

In one embodiment illustrated in FIGS. 5-7, the grip 24 may include a grip head 50 located at the end of the grip body 32 opposite the base 30. The grip head 50 may be configured for insertion into tissue while providing a sufficient amount of tissue grip to reduce, if not eliminate, inadvertent release from the tissue. The grip head may include one or more barbs configured to penetrate tissue and resist withdrawal of the grip from the tissue. In one embodiment, the grip head 50 may include four barbs 52a, 52b located at 90° positions about the end of the grip body. In this manner, the grip head may employ a cruciform configuration with a first pair of barbs 52a located along a first axis Y and a second pair of barbs 52b located along a second axis X. Such an arrangement may provide omnidirectional sliding resistance. However, the grip may include any number and location of barbs as should be apparent to one of skill in the art.

For some applications, it may be desirable to vary the location of the barbs along the length $L_1$ of the grip body. For example, it may be desirable to grip the tissue at different depths of penetration. In one embodiment, the grip head may include a first pair of barbs 52a located at a first distance $L_2$ along the grip body and a second pair of barbs 52b located at a second distance $L_3$ along the grip body which is different from the first distance. As should be appreciated, any number of barbs may be located at different locations along the barb body as should be apparent to one of skill in the art.

To facilitate locating and/or holding a tissue grip in position on the body portion, it may be desirable to provide the grip with a self-locating feature. In one embodiment illustrated in FIGS. 5-7, the grip may include a grip locator 54 configured for insertion into a pore 38 or other opening in the first or second layer of repair fabric. The size and/or shape of the grip locator may be selected to correspond to the pores of the repair fabric. As illustrated, the grip locator 54 may be configured as a boss protruding from the grip base 30 with the grip body extending from the locator. The grip locator 54 may protrude from a central region of the grip base, although other arrangements are contemplated.

Figure 8:
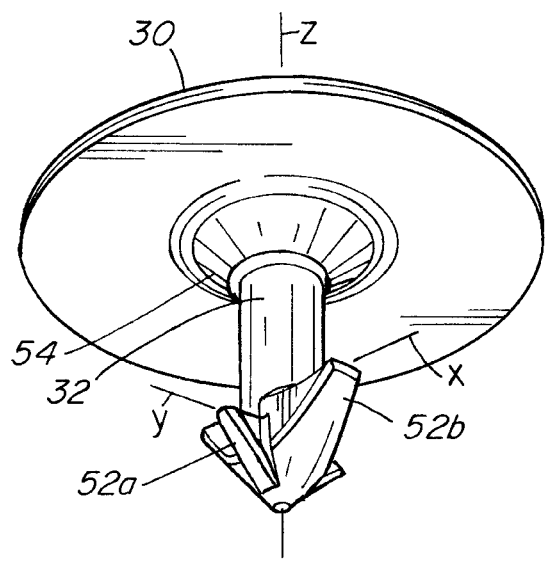
FIG. 8 is a perspective view of a tissue grip according to another illustrative embodiment.
Figure 9:
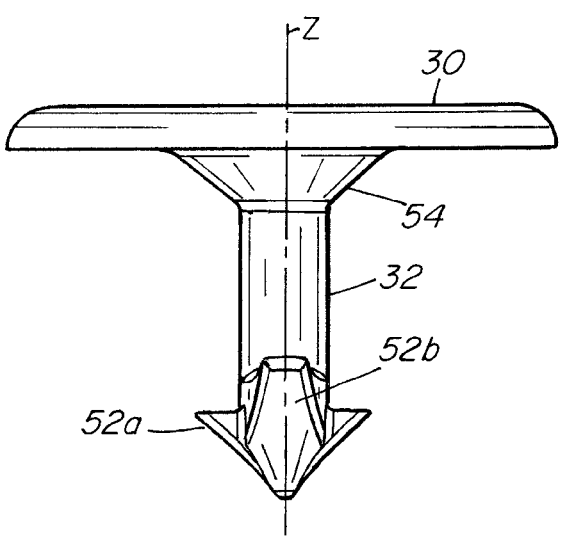
FIG. 9 is a side elevational view of the tissue grip of FIG. 8.

In one embodiment shown in FIG. 7, the grip locator 54 may have a cylindrical shape, although other shapes are contemplated. For example, in one embodiment illustrated in FIGS. 8-9, the grip locator 54 may have a conical or frusto-conical shape. As shown, the grip locator 54 may be tapered to decrease in size in a direction from the grip base 30 toward the grip body 32. Such an arrangement may facilitate insertion of the tissue grip into a pore 38 or other opening of the repair fabric. It should be understood, however, that the grip locator, if provided, may employ any suitable configuration as should be apparent to one of skill in the art.

Figure 10:
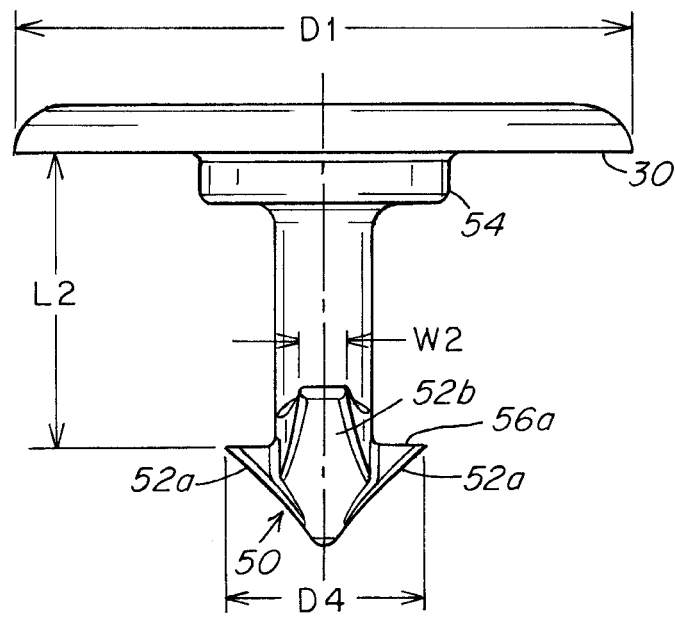
FIG. 10 is a side elevational view of the tissue grip of FIG. 7.
Figure 11:
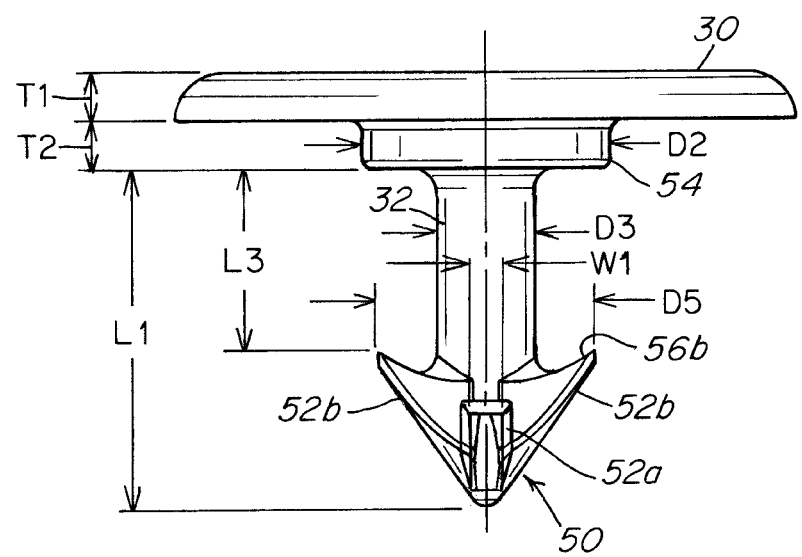
FIG. 11 is a side elevational view of the tissue grip of FIG. 10 rotated 90°.

In one illustrative embodiment shown in FIGS. 10-11, the grip base 30 may have a diameter $D_1$ of about 0.125 inches with a thickness $T_1$ of about 0.01 inches. The grip locator may have a diameter $D_2$ of about 0.05 inches with a thickness $T_2$ of about 0.01 inches. The grip body may have a length $L_1$ of about 0.08 inches extending from the surface of the grip base and a diameter $D_3$ of about 0.02 inches to about 0.035 inches. The grip head may include a first pair of barbs 52a with a grip surface 56a located a distance $L_2$ of about 0.06 inches from the grip base and a second pair of barbs 52b with a grip surface 56b located a distance $L_3$ of about 0.047 to about 0.05 inches from the grip base. The first pair of barbs 52a may have an outer diameter $D_4$ of about 0.04 inches and the second pair of barbs 52b may have an outer diameter $D_5$ of about 0.044 inches. The first pair of barbs 52a may have a width $W_1$ of about 0.006 inches and the second pair of barbs 52b may have a width $W_2$ about 0.01 inches.

In the embodiments described above, each grip may be fabricated as a single grip that is attached to the body portion of the prosthesis. For some applications, it may be desirable to fabricate and provide multiple interconnected grips for attachment to the body portion. For example, a grip arrangement including multiple grips may facilitate handling and assembly of the grips to the body portion in contrast to the smaller size of a single grip.

Figure 12:
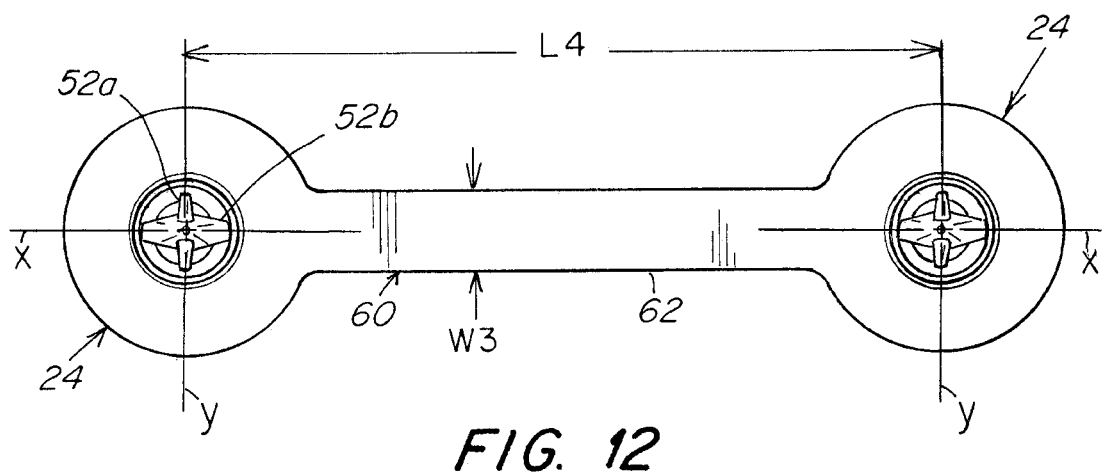
FIG. 12 is a top view of a grip assembly according to one illustrative embodiment.

In one embodiment illustrated in FIG. 12, a grip assembly 60 may include two (as shown) or more grips 24 connected together with an elongated coupling 62 extending therebetween. In one embodiment, the grip assembly may be fabricated as a unitary component. For example, the grip assembly may be a molded component fabricated from the same material. However, the grip assembly may be fabricated using any suitable process and may include multiple materials depending on the particular characteristics desired for the grips.

The coupling may be configured to provide a desired amount of support for handling the grips while also having a sufficient amount of flexibility to minimize any potential increase in the stiffness of the body portion. In one embodiment, the coupling 62 may have a thickness that corresponds to the thickness of the grip base 30 of the grips. The coupling 62 may be configured with a width $W_3$ of about 0.04 inches. The grips 24 may be configured with a center-to-center spacing $L_4$ of about 0.38 inches. It is to be understood that any suitable coupling arrangement and grip spacing may be utilized as should be apparent to one of skill in the art.

Figure 13:
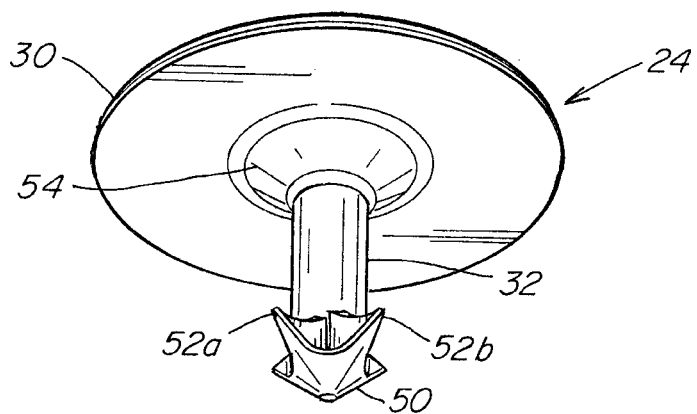
FIG. 13 is a perspective view of a tissue grip according to another illustrative embodiment.
Figure 14:
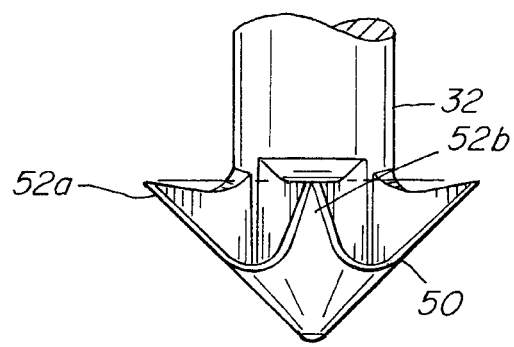
FIG. 14 is an enlarged side view of the grip head of FIG. 13 according to one embodiment.

For some applications, it may be desirable to employ a grip head 50 with a cruciform shape including barbs 52a, 52b having the same size and a grip surface 56 located the same distance from the grip base 30. FIGS. 13-14 illustrate one embodiment of such an arrangement. The grip head 50 may be utilized for a single grip, as illustrated in FIG. 13, or on each grip of a grip assembly, such as the grip assembly described above.

For some applications, it may be desirable to employ a grip head configured to reduce, if not eliminate, potential mesh entanglement during handling and/or delivery of the prosthesis. For example, and without limitation, it may be desirable to fold, roll, or otherwise collapse the prosthesis to facilitate delivery of the prosthesis during some surgical procedures. When collapsed, at least some of the grips may be placed into engagement with other portions of the prosthesis which could potentially lead to a grip becoming entangled with the prosthesis, particularly when the prosthesis is fabricated from a mesh fabric. Such entanglement may make it more difficult and require additional time for a surgeon to open the collapsed prosthesis after delivery to the surgical site.

Figure 15:
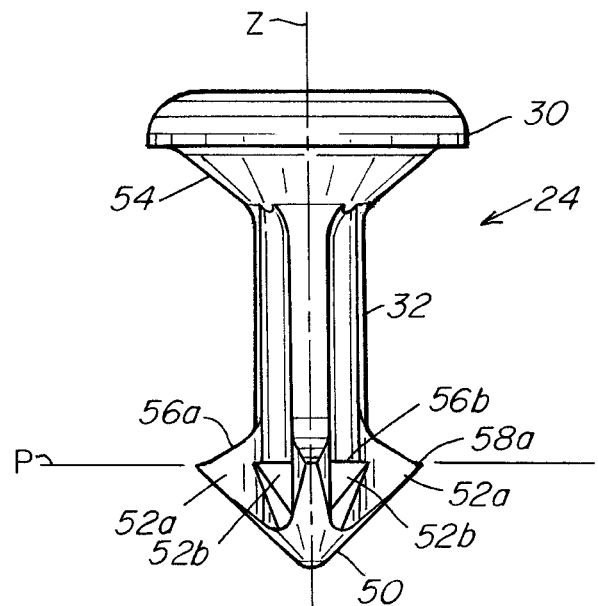
FIG. 15 is a side elevational view of a tissue grip according to another illustrative embodiment.
Figure 16:
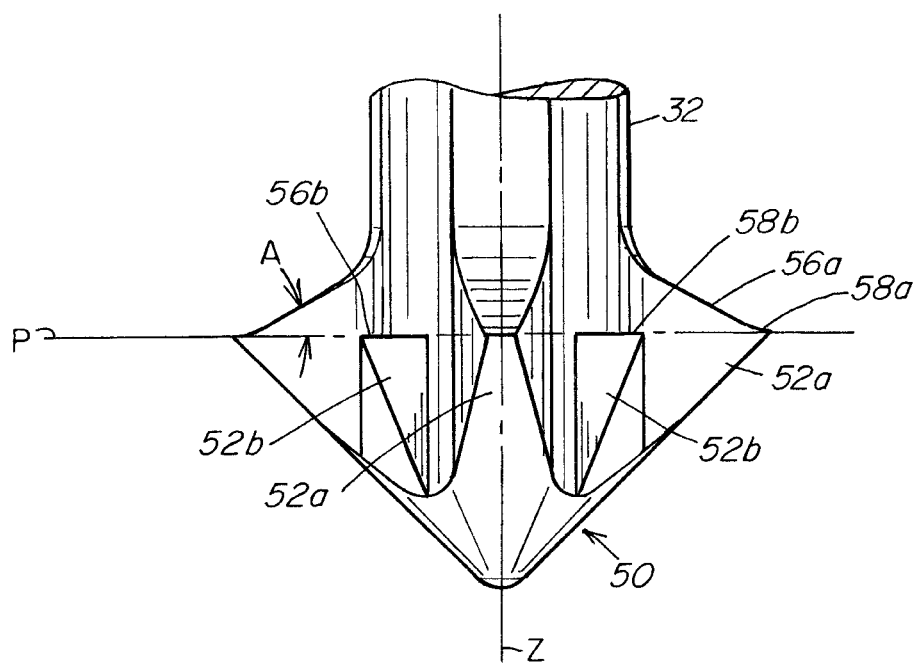
FIG. 16 is an enlarged side view of the grip head of FIG. 15 according to one embodiment.
Figure 17:
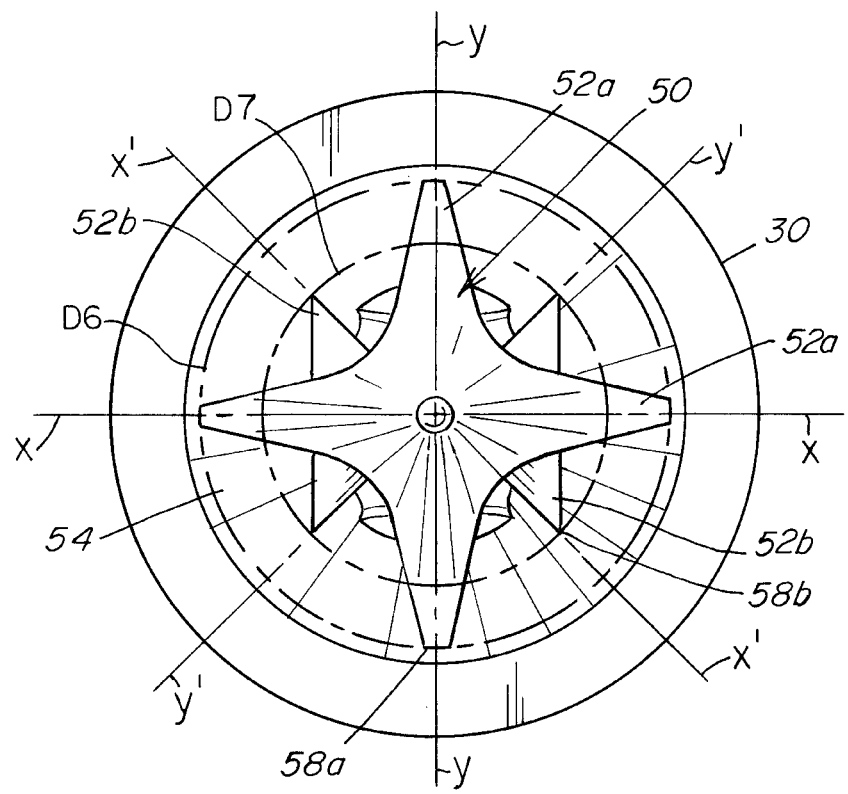
FIG. 17 is an enlarged bottom view of the grip head of FIGS. 15-16 according to one embodiment.

In one embodiment illustrated in FIGS. 15-17, the prosthesis may include grips 24 having a grip head 50 configured to grip tissue while also minimizing potential entanglement with the prosthesis. The grip head may include one or more primary barbs 52a configured to both grip tissue and minimize, if not eliminate, potential entanglement with the prosthesis. The grip head may also include one or more secondary barbs 52b configured solely to grip tissue. In this manner, the secondary barbs may enhance the grip of the barbs by providing additional traction while the primary barbs minimize potential entanglement.

The primary barbs 52a may be configured and arranged to shield the secondary barbs 52b from entanglement with the prosthesis while allowing the secondary barbs to grip tissue. In one embodiment, the secondary barbs 52b may be smaller in size as compared to the primary barbs 52a. As shown in FIG. 17, the grip head 50 may include four primary barbs 52a located along axes X, Y positioned 90° apart and four secondary barbs 52b located along axes X', Y' positioned 90° apart with the primary barbs being offset from the secondary barbs by about 45°. In this manner, each secondary barb 52b may be located between a pair of primary barbs 52a to minimize, if not prevent, engagement between the secondary barbs and the prosthesis, such as the filaments of a mesh prosthesis. However, it is to be appreciated that the grip head 50 may employ any number of primary barbs and/or secondary barbs positioned in any suitable arrangement as should be apparent to one of skill in the art.

The primary grip 52a may include a first grip surface 56a to grip tissue when placed against tissue while allowing the grip head 50 to release from the prosthetic material, such as mesh fabric, when placed against the prosthesis. In one embodiment, the first grip surface 56a may be configured with a ramp-like structure from which filaments of the prosthesis may be slid off and away from the grip head as the grip is being pulled away from the prosthesis. As shown, the first grip surface may be angled to slope inwardly from the outer tip 58a of the primary barb toward the grip body 32 and in a direction toward the grip base 30. In this manner, the first grip surface 56a may be oriented at an angle A so that filaments of the prosthesis located along the length of the grip body may be guided along the grip surface and off the grip head as the grip is pulled from the prosthesis.

In one embodiment, the first grip surface 56a may be oriented at an angle A of 30° relative to a plane P perpendicular to the longitudinal axis Z of the grip. However, other angles suitable for tissue grip and grip head release from the prosthesis may be employed as should be apparent to one of skill in the art. In this manner, varying the first grip surface angle may adjust the amount of tissue grip and grip head release. For example, a relatively large grip surface angle may enhance grip head release while reducing the amount of tissue grip, while a relatively small grip surface angle may reduce grip head release while increasing the amount of tissue grip.

The secondary grip 52b may include a second grip surface 56b configured to grip tissue when placed against tissue. In contrast to the angled configuration of the first grip surface 56a, the second grip surface may have a relatively flat configuration. In one embodiment, the second grip surface 56b may be oriented perpendicular to the longitudinal axis Z of the grip to provide a relatively higher degree of tissue grip as compared to the first grip surface 56a. If desired, other angles suitable for tissue grip may be employed as should be apparent to one of skill in the art. In this manner, varying the angle of the secondary grip surface may adjust the amount of tissue grip desired for the grip head.

In one embodiment as shown, the first grip surface 56a may be angled from the plane P of the second grip surface 56b. In this manner, the outer tips 58a of the primary grips 52a and the outer tips 58b of the secondary grips 52b may be coplanar. However, it is to be appreciated that the outer tip 58a of the primary grip 52a may be located in a plane offset from the tip 58b of the secondary grip 52b.

As indicated above, the primary grips 52a may be configured to shield the secondary grips 52b in a manner to minimize entanglement of the secondary grips with the prosthesis. In one embodiment shown in FIGS. 15-17, the first grip surface 56a may be located between the second grip surface 56b and the grip base 30. Additionally, the tips 58a of the primary grips 52a may extend in an outward radial direction from the grip body 32 a distance which is greater than the tips 58b of the secondary grips 52b. In this manner, features of the prosthesis, such as filaments of a mesh fabric, may be guided by the first grip surface in the outward radial direction away from the grip body and beyond the tip 58b of the secondary grip so that the filaments are guided around the secondary grips as the grip is pulled from the prosthesis. In one embodiment, the outer tips 58a of the first grips may be positioned along a circular diameter $D_6$ of 0.042 in and the outer tips 58b of the secondary tips may be positioned along a circular diameter $D_7$ of 0.031 in. However, it is to be appreciated that other arrangements of the outer tips of the barbs of the grip head may be employed as should be appreciated by one of skill in the art.

The grip head 50 may be utilized for a single grip, as illustrated in FIG. 15, or on each grip of a grip assembly, such as the grip assembly described above.

As indicated above, the tissue grip may employ various configurations to provide a desired amount of grip for holding the prosthesis in place against tissue. The grip described above may be considered as having a cruciform configuration. Examples of other non-limiting grip configurations are described below in connection with FIGS. 18-21.

Figure 18:
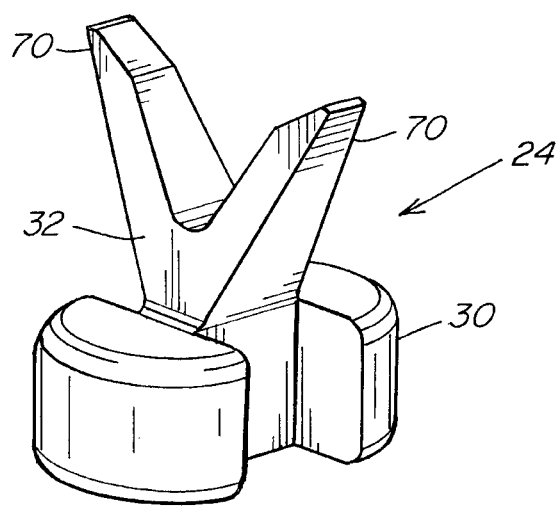
FIG. 18 is a perspective view of a tissue grip with a V-shaped configuration according to another illustrative embodiment.

FIG. 18 illustrates an embodiment of a grip having a multi-prong configuration. As shown, the grip body 32 may include a pair of prongs 70 extending from the grip base 30. The prongs 70 may be arranged in a V-shaped configuration for penetration into tissue.

Figure 19:
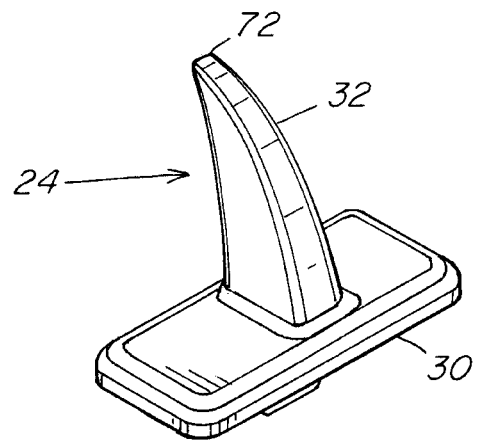
FIG. 19 is a perspective view of a tissue grip with a crescent shaped configuration according to another illustrative embodiment.

FIG. 19 illustrates an embodiment of a grip having a crescent configuration. As shown, the grip body 32 may have a crescent shape extending from the grip base 30. The grip body 32 decreases in size in a direction from the base 30 toward its tip 72 for penetration into tissue.

Figure 20:
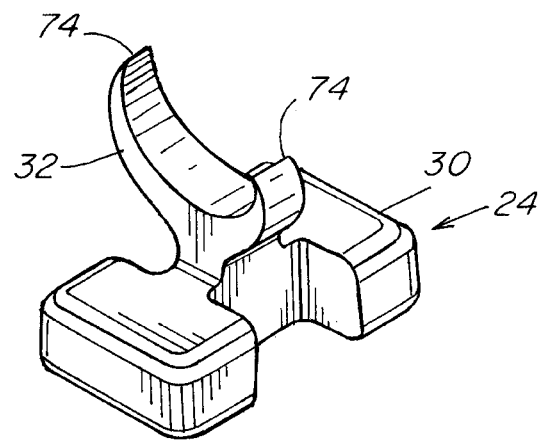
FIG. 20 is a perspective view of a tissue grip with a claw-like configuration according to another illustrative embodiment.

FIG. 20 illustrates an embodiment of a grip having a claw-like configuration. As shown, the grip body 32 employ a C-shaped configuration with a pair of tips 74 for penetrating tissue. As shown, the grip body 32 may be oriented relative to the grip base 30 with the tips extending in a direction away from the grip base.

Figure 21:
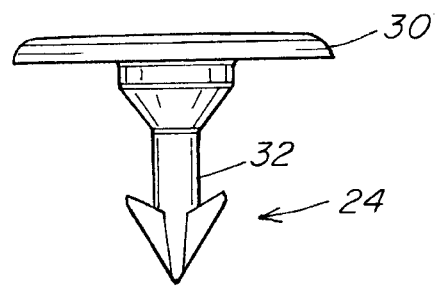
FIG. 21 is a side elevational view of a tissue grip with an arrowhead configuration according to another illustrative embodiment.

FIG. 21 illustrates an embodiment of a grip having an arrowhead configuration. As shown, the grip body 32 extends from the grip base 30. The grip body 32 include an arrowhead with a pair of oppositely extending barbs for penetrating and gripping tissue.

As illustrated in FIGS. 1-4, the body portion 22 may be a preformed, non-planar patch with a 3-dimensional curved shape. In one embodiment, the body portion 22 may have a shape corresponding to the 3DMAX Light Mesh or 3DMAX Mesh, available from C. R. Bard, and described in one or more of U.S. Pat. Nos. 6,723,133, 6,740,122 and 6,740,122. In this manner, the prosthesis may be particularly suited for fitting and mending defects to the inguinal anatomy. However, it is to be understood that the prosthesis may employ other configurations as should be apparent to one of skill in the art. For example, and without limitation, the patch may have planar or other non-planar configurations suitable for a particular procedure employed for mending a defect. Moreover, the prosthesis may be provided as a planar sheet of self-gripping repair fabric that may be selectively trimmed by a surgeon to any desired size and shape for the particular procedure.

As indicated above, the prosthesis may employ any arrangement of grips to provide a desired amount of grip and traction for a particular application.

Figure 22:
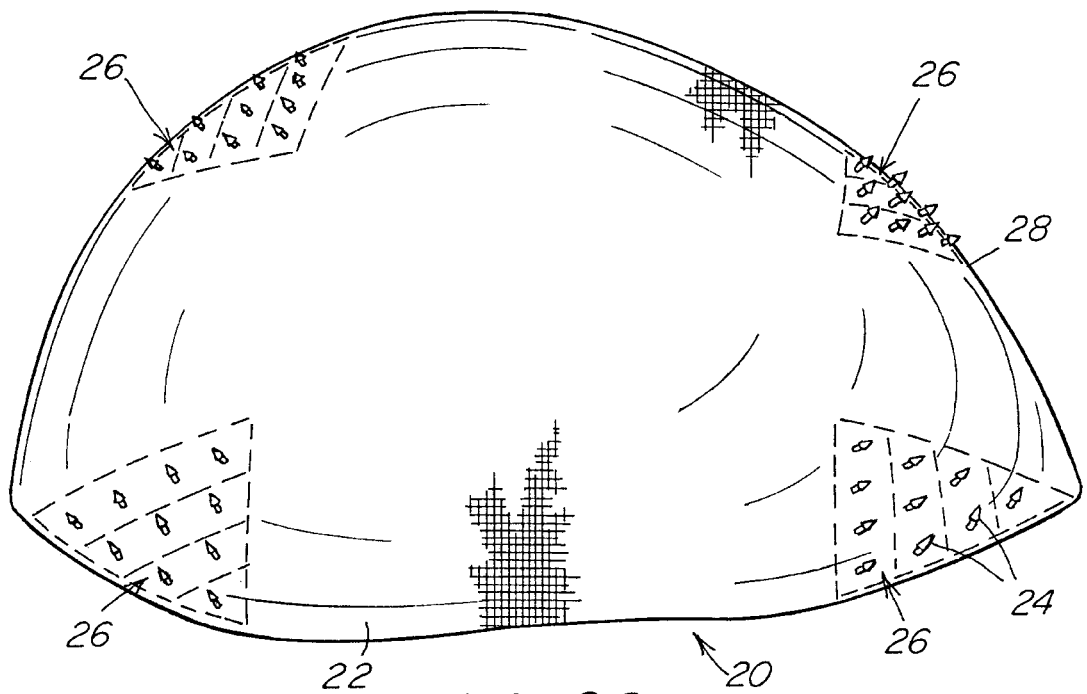
FIG. 22 is a top view of an implantable prosthesis with a grip arrangement according to one embodiment.

FIG. 22 illustrates an embodiment of a 3D curved prosthesis 20 including four separate grip regions 26, as compared to three grip regions as shown in FIGS. 1-4, located in proximity to the outer periphery 28 of the body portion 22. As shown, each group or grip region 26 may include multiple rows and/or columns of grips 24.

Figure 23:
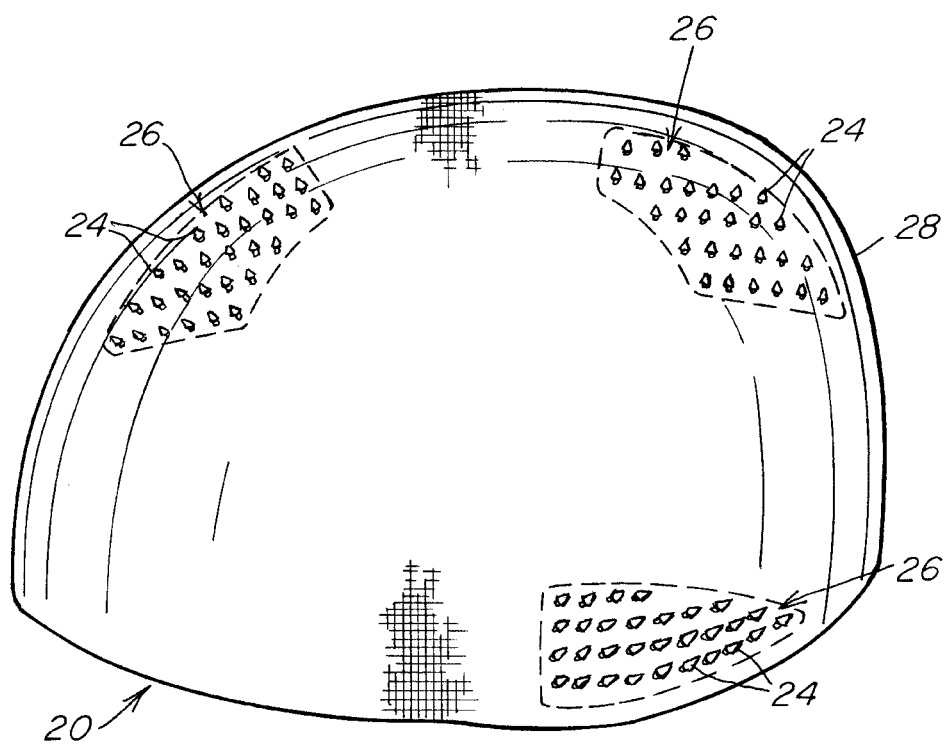
FIG. 23 is a top view of an implantable prosthesis with a grip arrangement according to one embodiment.

FIG. 23 illustrates an embodiment of a 3D curved prosthesis 20 including three separate grip regions 26 located in proximity to the outer periphery 28 of the body portion 22. A pair of grip regions may be located on upper medial and lateral portions of the prosthesis, and a grip region may be located on a lower medial portion of the prosthesis. As shown, each group or grip region 26 may include multiple rows and/or columns of grips 24. Each grip region on the upper medial and lateral portions may have a semi-annular periphery. The grip region on the lower medial portion may have a triangular periphery.

Figure 24:
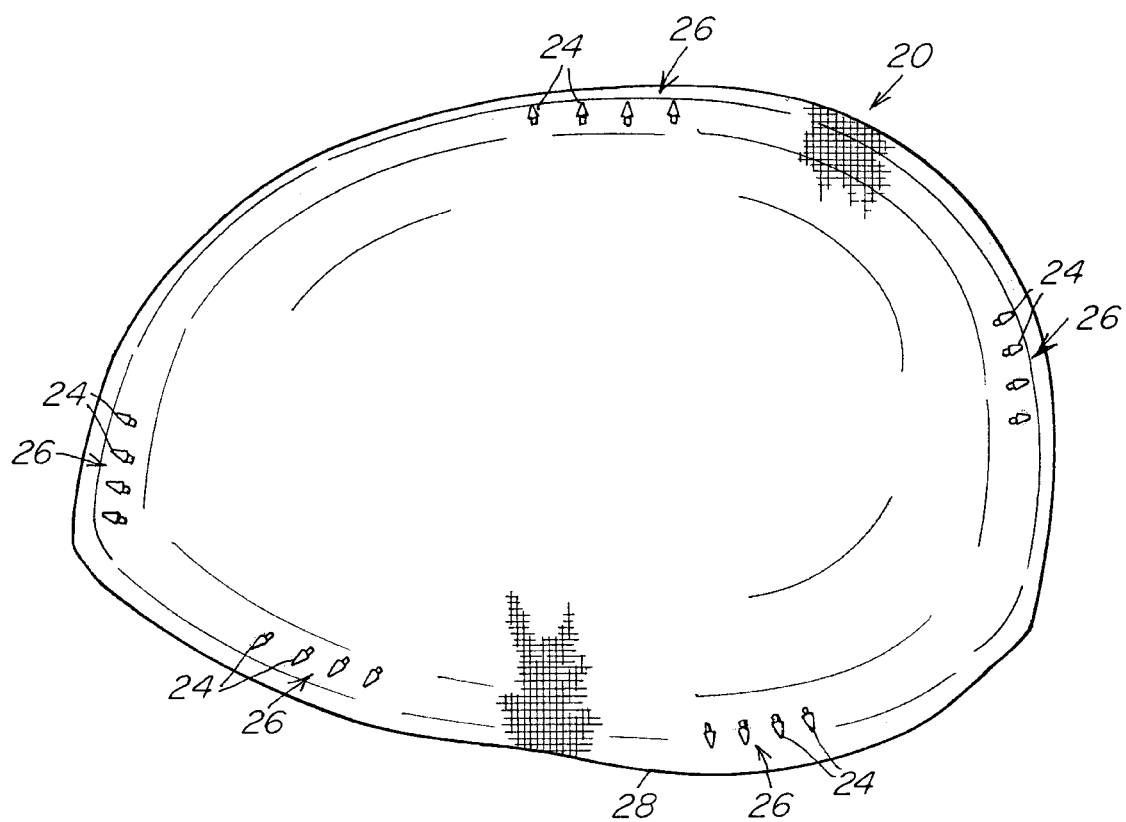
FIG. 24 is a top view of an implantable prosthesis with a grip arrangement according to one embodiment.

FIG. 24 illustrates an embodiment of a 3D curved prosthesis 20 including separate groups of grips 24 located along the outer periphery 28 of the body portion 22. As shown, each group or grip region 26 may include a single row of grips 24.

Figure 25:
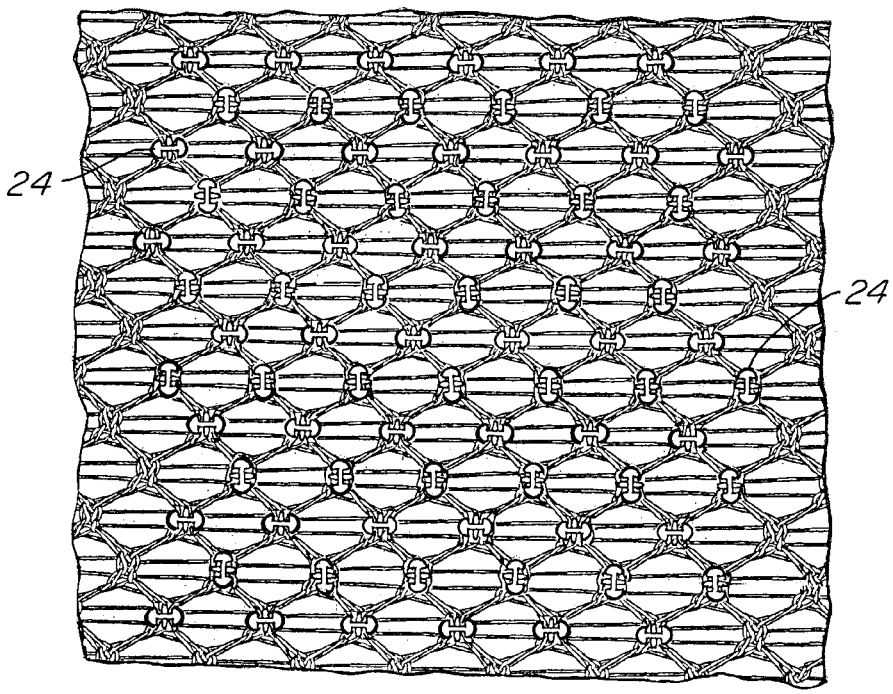
FIG. 25 is an illustration of a grip arrangement according to another embodiment.

FIG. 25 illustrates an embodiment of a layer of repair fabric including grips 24 uniformly distributed across the fabric. The fabric may be preformed into a configuration for use as a prosthesis or may be selectively trimmed into a desirable configuration for use as a prosthesis or a portion of a prosthesis, such as a second layer described above. As shown, the grips may be mounted to the fabric in at least two different orientations to provide a desired grip or traction properties for the prosthesis. For example, and without limitation, the prosthesis may include grips, such as the grips illustrated in FIGS. 18-21, which individually provide bidirectional traction. Mounting the grips in alternating 90° orientations may provide omnidirectional traction for the prosthesis. The particular spacing and orientation may be selected to provide the desired grip and/or traction.

The repair fabric may employ a knit construction that provides openings or pores to allow tissue infiltration to incorporate the prosthesis. The repair fabric may also have sufficient flexibility to promote an easy reduction in size for entry into the subject. In this manner, the flexible fabric may be collapsed into a slender configuration, such as a roll, which can be supported in, and advanced through, a narrow laparoscopic cannula for use in laparoscopic or robotic procedures.

In one embodiment, the prosthesis 20 may be formed from one or more layers of knitted mesh fabric. When implanted, the mesh promotes rapid tissue or muscle ingrowth into and around the mesh structure. Examples of surgical materials which may be utilized for the layers and are suitable for tissue or muscle reinforcement and defect correction include, but are limited to, BARD Mesh (available from C. R. Bard, Inc.), BARD Soft Mesh (available from C. R. Bard, Inc.), SOFT TISSUE PATCH (microporous ePTFE—available from W. L. Gore & Associates, Inc.); SURGIPRO (available from US Surgical, Inc.); TRELEX (available from Meadox Medical); PROLENE and MERSILENE (available from Ethicon, Inc.); and other mesh materials (e.g., available from Atrium Medical Corporation). Absorbable or resorbable materials, including PHASIX Mesh (available from C. R. Bard, Inc.), polyglactin (VICRYL—available from Ethicon, Inc.) and polyglycolic acid (DEXON—available from US Surgical, Inc.), may be suitable for applications involving temporary correction of tissue or muscle defects. Collagen materials such as COOK SURGISIS, available from Cook Biomedical, Inc. may also be used. It also is contemplated that the mesh fabric may be formed from multifilament yarns and that any suitable method, such as knitting, weaving, braiding, molding and the like, may be employed to form the mesh material.

In one embodiment, the grips may be formed of a resorbable material. In this manner, the grips provide a desired level of tissue grip for initial placement and positioning of the prosthesis. The grips eventually become rebsorbed by the body at which time the prosthesis has become sufficiently integrated with the tissue. Examples of rebsorbable materials which may be utilized for the grips include, but are not limited to, PLG (L-lactide/glycolide) or PLA (polylactic acid) polymers. For some applications, it may be desirable to utilize non-resorbable grips. An example of non-rebsorbable material which may be utilized for the grips includes, but is not limited to, polypropylene. It is to be appreciated that other suitable biocompatible materials, resorbable or non-resorbable, may be used for the grips as should be apparent to one of skill in the art.

In one embodiment, the grips may be fabricated using an injection molding process. However, any suitable manufacturing process may be used to fabricate the grips as should be apparent to one of skill in the art. For example, and without limitation, the grips may be fabricated using 3D printing and machining processes.

Examples

The following examples are illustrative only and are not intended to limit the scope of the present invention.

Traction force was evaluated for various grip arrangements and compared to a known mesh fabric. Testing methodology is described below with results provided in Table 1. The average results are reported from testing ten samples of each configuration.

A fresh, square coupon of porcine tissue, kept at room temperature, was prepared and placed in a test fixture. The porcine tissue coupon measured 2.7 inches×3.5 inches with a minimum thickness of 0.25 inches. An approximately 1 inch×1 inch test sample (unless indicated otherwise below) of a self-gripping mesh configuration was placed, barb side down, on top of and centered on the porcine tissue sample. A free weight was set on top of the mesh sample for about 3 seconds and then removed. The free weight was approximately 1 lb to 3 lb. The mesh sample was allowed to rest/settle on the porcine tissue sample, at room temperature, undisturbed for 1 minute before initiating the test.

Using a force gauge, such as a Mark-10 tensiometer gauge, with a gripping attachment to secure a portion of the mesh sample, a traction force was applied to the mesh in a single direction along the plane defined by the contact area between the mesh sample and the porcine tissue sample. The mesh was oriented so that the grips were pulled in the direction of the barbs or other grip features. The procedure was repeated for ten mesh samples of the same configuration.

Test samples were provided with different grip configurations and arrangements of grips. The grip arrangements of the test samples are illustrated in FIGS. 26-31. The direction of applied force is shown as arrow F.

Figure 26:
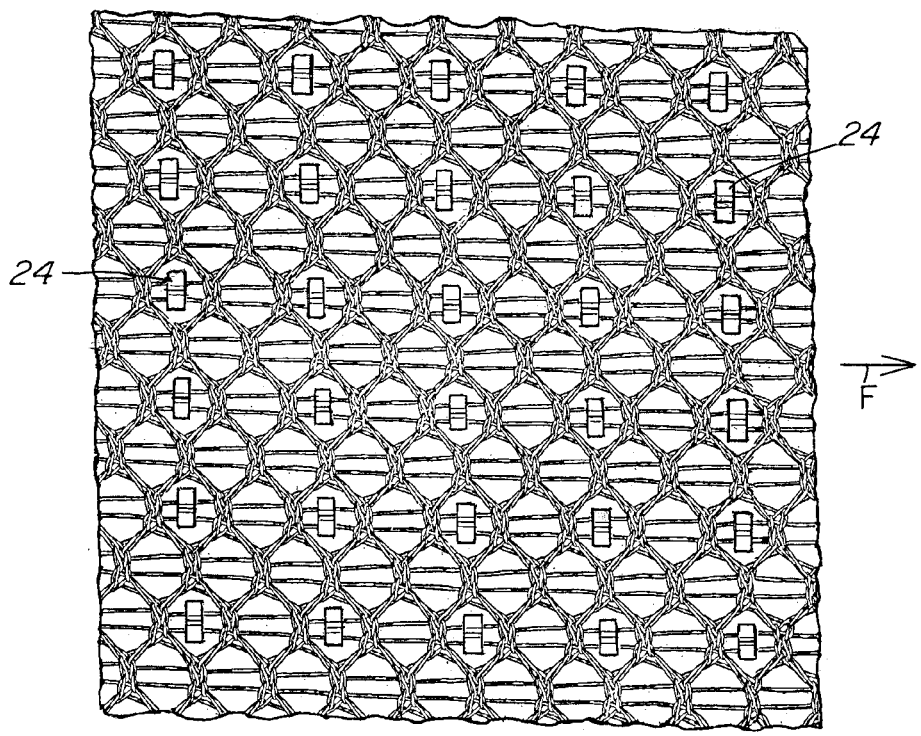
FIG. 26 is an illustration of a grip arrangement according to another embodiment.

FIG. 26 illustrates a grip arrangement including grips located every other space and every other row. This arrangement was tested for grip configurations illustrated in FIGS. 18-21.

Figure 27:
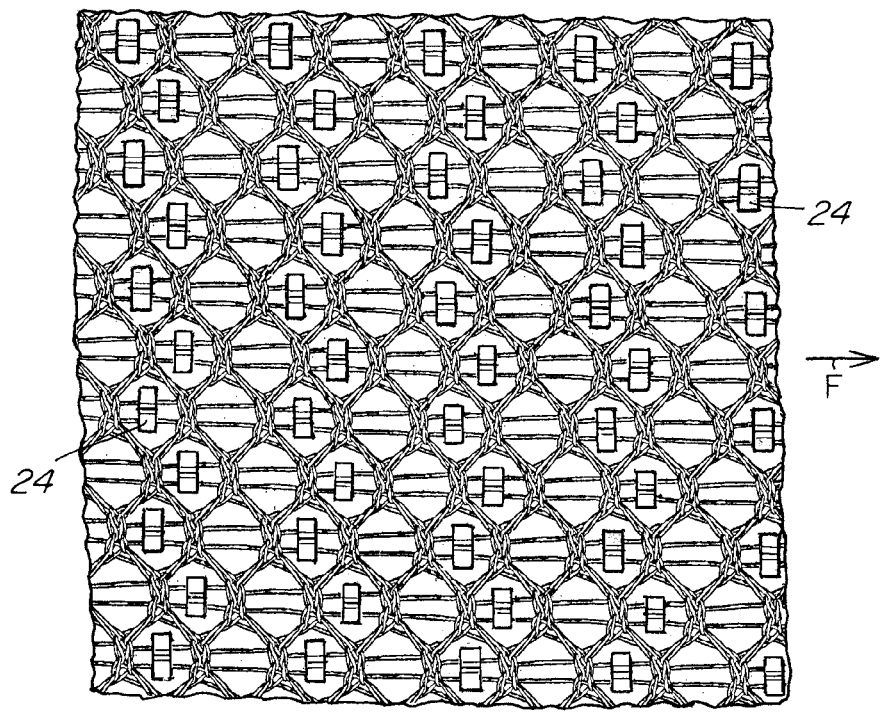
FIG. 27 is an illustration of a grip arrangement according to another embodiment.

FIG. 27 illustrates a grip arrangement including grips located every other space and every row. This arrangement was tested for grip configurations illustrated in FIGS. 18-21.

Figure 28:
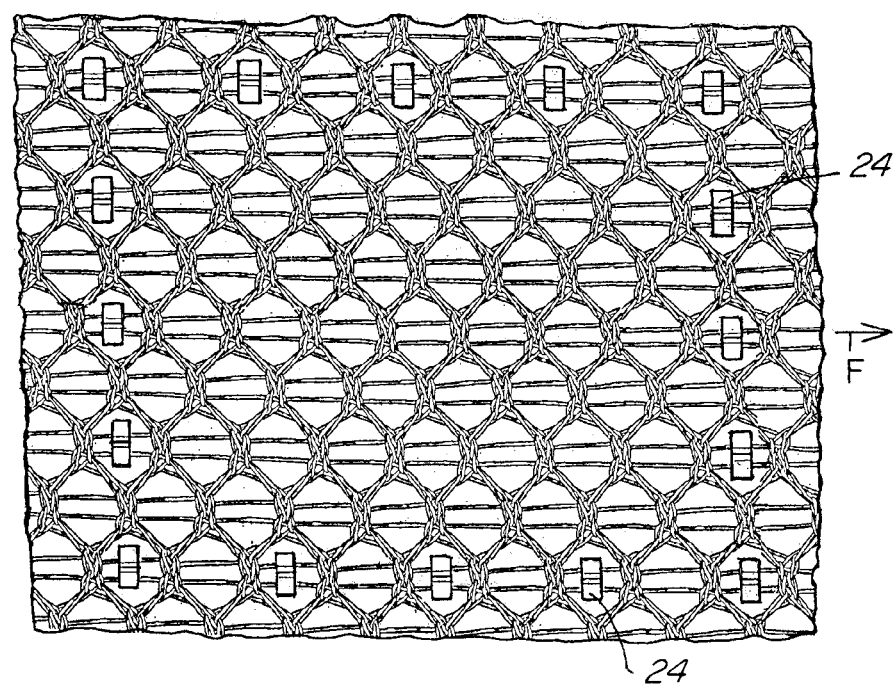
FIG. 28 is an illustration of a grip arrangement according to another embodiment.

FIG. 28 illustrates a grip arrangement including grips positioned in a 5×5 square. This arrangement was tested for grip configurations illustrated in FIGS. 18-21.

Figure 29:
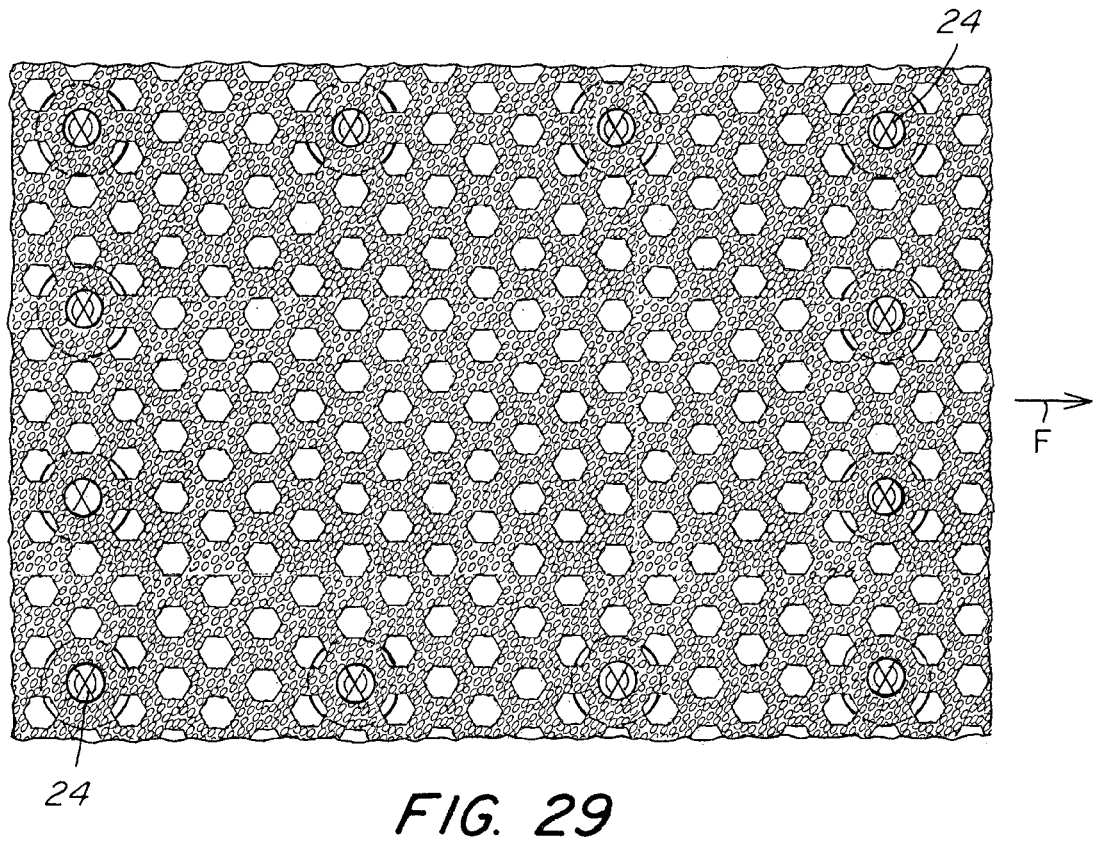
FIG. 29 is an illustration of a grip arrangement according to another embodiment

FIG. 29 illustrates a grip arrangement including grips positioned in a 4×4 square. This arrangement was tested for the grip configuration illustrated in FIG. 21.

Figure 30:
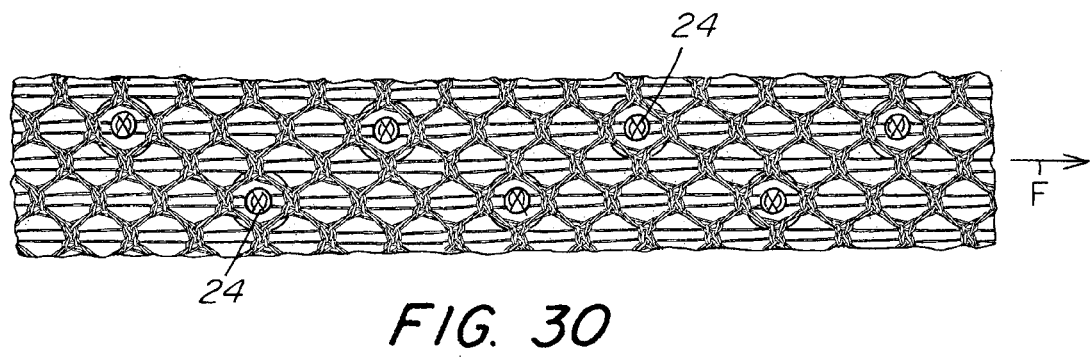
FIG. 30 is an illustration of a grip arrangement according to another embodiment.

FIG. 30 illustrates a grip arrangement including grips located in two rows with four grips provided in one row and three grips provided in the other row. This arrangement was tested for the grip configuration illustrated in FIG. 21.

Figure 31:
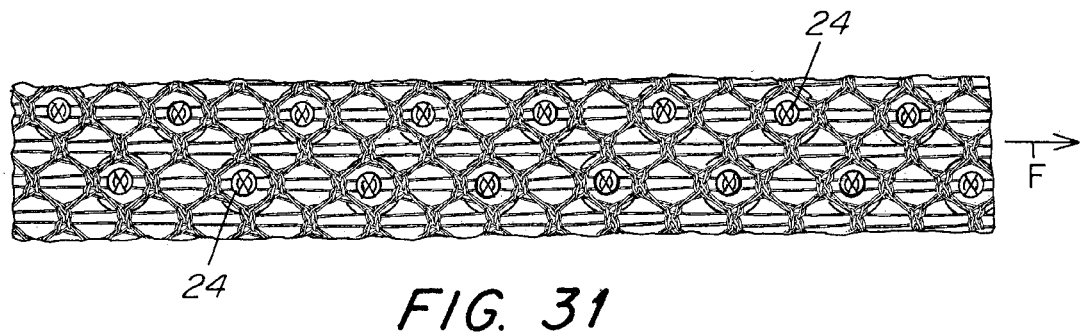
FIG. 31 is an illustration of a grip arrangement according to another embodiment.

FIG. 31 illustrates a grip arrangement including grips located in two rows with eight grips provided in each row. This arrangement was tested for grip configurations illustrated in FIGS. 18-21.

Figure 32:
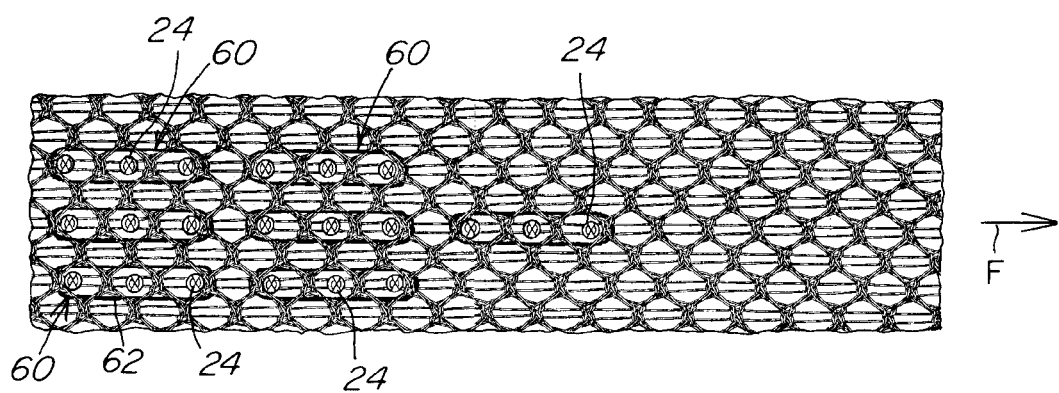
FIG. 32 is an illustration of a grip arrangement according to another embodiment.

FIG. 32 illustrates a grip arrangement including seven grip arrays located in three rows with three arrays provided in a center row flanked by rows with two arrays. The grip arrays were located within a test sample area of approximately 1.7 inches×0.8 inches. Each array includes three grips for a total of twenty-one grips with nine grips located along the central row and six grips located along each row flanking the center row. This arrangement was tested for the grip configuration illustrated in FIGS. 15-17. This arrangement provided an average traction force of 0.68 lbf.

For ease of presenting the test results for the other arrangements, the grip configurations are referred to as Grip A (FIG. 18), Grip B (FIG. 19), Grip C (FIG. 20) and Grip D (FIG. 21). Similarly, the grip arrangements are referred to as Arrangement 1 (FIG. 26), Arrangement 2 (FIG. 27), Arrangement 3 (FIG. 28), Arrangement 4 (FIG. 29), Arrangement 5 (FIG. 30), and Arrangement 6 (FIG. 31).

TABLE 1

| Test Sample | Average Traction Force (psi) |
| --- | --- |
| Covidien ProGrip Mesh | 0.275 |
| Grip A, Arrangement 1 | 0.285 |
| Grip A, Arrangement 2 | 0.335 |
| Grip B, Arrangement 1 | 0.3 |
| Grip B, Arrangement 2 | 0.26 |
| Grip C, Arrangement 1 | 0.285 |
| Grip C, Arrangement 2 | 0.39 |
| Grip A, Arrangement 3 | 0.335 |
| Grip B, Arrangement 3 | 0.21 |
| Grip C, Arrangement 3 | 0.315 |
| Grip D, Arrangement 4 | 0.49 |
| Grip D, Arrangement 5 | 0.32 |
| Grip A, Arrangement 6 | 0.335 |
| Grip B, Arrangement 6 | 0.365 |
| Grip C, Arrangement 6 | 0.415 |

For purposes of this patent application and any patent issuing thereon, the indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

The foregoing description of various embodiments are intended merely to be illustrative thereof and that other embodiments, modifications, and equivalents are within the scope of the invention recited in the claims appended hereto.

What is claimed is:

1. A method of fabricating an implantable prosthesis for implantation in a person, the method comprising acts of:
   (a) providing a first layer of biologically compatible repair fabric including a first surface and a second surface opposite the first surface, the first layer having a 3-dimensional curved configuration adapted to fit an inguinofemoral anatomy of a person;
   (b) attaching a plurality of preformed tissue grips to the first layer of repair fabric to form a self-gripping prosthesis prior to implantation, the plurality of preformed tissue grips being fabricated independent of the first layer, each preformed tissue grip including a grip base and a grip body extending from the grip base, each of the plurality of preformed tissue grips being attached to the first layer by passing the grip body through the first layer to protrude beyond the first surface and positioning the grip base adjacent the second surface; and
   (c) attaching a second layer of biologically compatible repair fabric to the second surface of the first layer to secure the plurality of preformed tissue grips to the first layer.

2. The method according to claim 1, wherein act (c) includes capturing the grip base between the first layer and the second layer.

3. The method according to claim 1, wherein each preformed tissue grip includes a grip head having a cruciform configuration.

4. The method according to claim 1, wherein the first surface has an outwardly facing curvature and the second surface has an inwardly facing curvature.

5. The method according to claim 1, wherein the plurality of preformed tissue grips are integrated with the second layer.

6. The method according to claim 5, wherein the plurality of preformed tissue grips are molded to the second layer.

7. The method according to claim 1, wherein act (b) includes distributing the plurality of preformed tissue grips in a plurality of distinct grip regions.

8. The method according to claim 7, wherein each grip region includes multiple preformed tissue grips.

9. The method according to claim 7, wherein at least one grip region has a triangular arrangement of preformed tissue grips or a semi-annular arrangement of preformed tissue grips.

10. The method according to claim 7, wherein each grip region has a triangular arrangement of preformed tissue grips.

* * * * *